US008232072B2

(12) United States Patent
Kalnik et al.

(10) Patent No.: US 8,232,072 B2
(45) Date of Patent: Jul. 31, 2012

(54) SMOKING CESSATION KIT AND METHOD

(75) Inventors: Matthew Kalnik, Bethesda, MD (US); Matthew Hohenboken, Potomac, MD (US); Paul Kessler, Hagerstown, MD (US); Ali Fattom, Rockville, MD (US); Raafat Fahim, Boca Raton, FL (US); Leslie Hudson, Bend, OR (US)

(73) Assignee: Nabi Biopharmaceuticals, Rockville, MD (US)

( * ) Notice: Subject to any disclaimer, the term of this patent is extended or adjusted under 35 U.S.C. 154(b) by 190 days.

(21) Appl. No.: 12/481,420

(22) Filed: Jun. 9, 2009

(65) Prior Publication Data

US 2010/0040638 A1 Feb. 18, 2010

Related U.S. Application Data

(60) Provisional application No. 61/129,247, filed on Jun. 13, 2008.

(51) Int. Cl.
*G01N 33/53* (2006.01)
*C07K 1/04* (2006.01)
(52) U.S. Cl. ...... 435/7.92; 435/7.1; 530/403; 424/175.1
(58) Field of Classification Search .................. None
See application file for complete search history.

(56) References Cited

U.S. PATENT DOCUMENTS

| 6,232,082 | B1 | 5/2001 | Ennifar et al. | |
| 6,518,031 | B2* | 2/2003 | Ennifar et al. | 435/7.1 |
| 7,052,854 | B2 | 5/2006 | Melker et al. | |
| 7,247,502 | B2 | 7/2007 | Ennifar et al. | |
| 7,776,620 | B2* | 8/2010 | Ennifar et al. | 436/544 |
| 2011/0002957 | A1* | 1/2011 | Ennifar et al. | 424/193.1 |
| 2011/0064750 | A1 | 3/2011 | Fahim et al. | |

FOREIGN PATENT DOCUMENTS

GB 2 333 869 8/1999

OTHER PUBLICATIONS

U.S. Appl. No. 12/926,910, filed Dec. 16, 2010, Fahim et al.
International Search Report issued on Dec. 4, 2009 in application No. PCT/US2009/046769.
International Search Report issued on Nov. 9, 2010 in application No. PCT/US2010/043748 (corresponding to US 2011/0064750).
Anonymous, "Nichtraucher warden, Sie können es schaffen" [Online] 2007, XP002546391, retrieved from the Internet: http://nicotinell.novartis-consumer-health.de/1347—{index.htm{cube root}, retrieved on Sep. 18, 2009.
Maurer et al., "Vaccination against nicotine: an emerging therapy for tobacco dependence," Expert Opin. Investig. Drugs, vol. 16, No. 11, pp. 1775-1783, 2007.
Rennard et al., "Abstract 3712: A Radomized Placebo-Controlled Trial of a Conjugate Nicotine Vaccine (NicVAX®) in Smokers Who Want to Quit: 12 Month Results," Circulation, vol. 116, p. 844, 2007.
Hatsukami et al., "Safety and immunogenicity of a nicotine conjugate vaccine in current smokers," Clinical Pharmacology & Therapeutics, vol. 78, No. 5, pp. 456-467, 2005.
Boyd, "NicVAX™, Aid to Smoking Cessation, nicotine vaccine," Drugs of the Future, vol. 31, No. 3, pp. 203-205, Mar. 2006.
Moreno et al., "Immunopharmacotherapy: Vaccination strategies as a treatment for drug abuse and dependence," Pharmacology, Biochemistry and Behavior, vol. 92. pp. 199-205, 2009.
Pentel et al., "A Nicotine Conjugate Vaccine Reduces Nicotine Distribution to Brain and Attenuates Its Behavioral and Cardiovascular Effects in Rats," Pharmacology, Biochemistry and Behavior, vol. 65, No. 1, pp. 191-198, 2000.
Roiko et al., "Combined Active and Passive Immunization Enhances the Efficacy of Immunotherapy against Nicotine in Rats," The Journal of Pharmacology and Experimental Therapeutics, vol. 325, No. 2, pp. 985-993, 2008.
Rose, "Disrupting Nicotine Reinforcement," Ann. N.Y. Acad. Sci., vol. 1141, pp. 233-256, 2008.
Bevins et al., "Vaccines to combat smoking," Expert Opin. Biol. Ther., vol. 8, No. 4, pp. 379-383, 2008.
Maurer et al., "A therapeutic vaccine for nicotine dependence: preclinical efficacy, and phase I safety and immunogenicity," Eur. J. Immunol., vol. 35, pp. 2031-2040, 2005.
Frishman et al., "Nicotine and Non-nicotine Smoking Cessation Pharmacotherapies," Cardiology in Review, vol. 14, No. 2, pp. 57-73, Mar./Apr. 2006.
Siu et al., "Non-Nicotine Therapies for Smoking Cessation," Annu. Rev. Pharmacol. Toxicol., vol. 47, pp. 541-564, 2007.
Nides, "Update on Pharmacologic Options for Smoking Cessation Treatment," The American Journal of Medicine, vol. 121 (4A), pp. 520-531, 2008.
Corunuz et al., "A Vaccine against Nicotine for Smoking Cessation: A Randomized Controlled Trial," PLoS One, vol. 3, Issue 6, e2547, Jun. 2008.
Frishman, "Smoking cessation pharmacotherapy," Therapeutic Advances in Cardiovascular Disease, pp. 1-22, 2009.
Carrozzi et al., "Pharmacotherapy for smoking cessation," Therapeutic Advances in Respiratory Disease, vol. 2, No. 5, pp. 301-317, 2008.
Henningfield et al., "Pharmacotherapy for Nicotine Dependence," CA Cancer J. Clin, vol. 55, pp. 281-299, 2005.
Foulds et al., "Advances in pharmacotherapy for tobacco dependence," Expert Opinion, vol. 9, No. 1, pp. 39-53, 2004.
Roiko et al., "Passive immunization with a nicotine-specific monoclonal antibody decreases brain nicotine levels but does not precipitate withdrawal in nicotine-dependent rats," Pharmacology, Biochemistry and Behavior, vol. 93, pp. 1050111, 2009.
Sanderson et al., "Immunization to nicotine with a peptide-based vaccine composed of a conformationally biased agonist of C5a as a molecular adjuvant," International Immunotherapy, vol. 3, pp. 137-146, 2003.
Garwood et al., "Emerging pharmacotherapies for smoking cessation," Am. J. Health-Syst Pharm., vol. 64, pp. 1693-1698, Aug. 15, 2007.
Schachter et al., "Targeted therapies for the prevention of lung cancer," Drugs of Today, vol. 43, No. 12, pp. 897-936, 2007.

(Continued)

*Primary Examiner* — Shafiqul Haq
(74) *Attorney, Agent, or Firm* — Foley & Lardner LLP

(57) ABSTRACT

Described are smoking cessation devices and kits for determining an advantageous time for a subject to quit smoking, and/or for extending the duration of smoking abstinence, based on serum levels of anti-nicotine antibodies. Related methods are also described.

18 Claims, 14 Drawing Sheets

OTHER PUBLICATIONS

Nabi Biopharmaceuticals, "Nabi Biopharmaceuticals to Present at Noble Financial's Fifth Annual Equity Conference," News Release, Jun. 2, 2009 (presentation on Jun. 8, 2009), www.nabi.com (accessed May 12, 2011).

Nabi Biopharmaceuticals, "Nabi Biopharmaceuticals Announces Encouraging Results from NicVAX™ PhaseI/II Clinical Trial in Smokers and Non-smokers," News Release, www.nabi.com, 2004.

Nabi Biopharmaceuticals, "Nabi Biopharmaceuticals Announces Positive Phase II Results with NicVAX™ for Smoking Cessation," News Release, www.nabi.com, 2004.

Nabi Biopharmaceuticals, "Nabi Biopharmaceuticals Announces Completion of NicVAX™ Phase II Clinical Trial Enrollment," News Release, www.nabi.com, Jul. 20, 2005 (accessed May 11, 2011).

Nabi Biopharmaceuticals, "Nabi Biopharmaceuticals Receives NIDA Grant to Fund NicVAX™ Development," News Release, www.nabi.com, Sep. 12, 2005.

Nabi Biopharmaceuticals, "Nabi Biopharmaceuticals Announces U.S. Fast Track Designation for NicVAX™," News Release, www.nabi.com, Mar. 9 (accessed May 11, 2011).

Nabi Biopharmaceuticals, "Nabi Biopharmaceuticals Initiates Phase IIB Proof-in-Concept Study for NicVAX," News Release, www.nabi.com, May 24, 2006 (accessed May 11, 2011).

Nabi Biopharmaceuticals, "Nabi Biopharmaceuticals Completes Enrollment in NicVAX™ Phase Phase IIB 'Proof-in-concept' Clinical Trial," News Release, www.nabi.com, Oct. 12, 2006 (accessed May 11, 2011).

Nabi Biopharmaceuticals, "Nabi Biopharmaceuticals Announces Positive Results of Phase IIb trial of NicVAX," News Release, www.nabi.com, May 2, 2007 (accessed Nov. 8, 2010).

Nabi Biopharmaceuticals, "Nabi Biopharmaceuticals Announces Continued Positve NicVAX Phase 2b Data at Nine Months," News Release, www.nabi.com, Sep. 5, 2007 (accessed Nov. 8, 2010).

Nabi Biopharmaceuticals, "Nabi Biopharmaceuticals Announces Positive Interim Results of NicVax Immunogenicity Study," News Release, www.nabi.com, Jul. 23, 2007 (accessed May 12, 2011).

Nabi Biopharmaceuticals, "Nabi Biopharmaceuticals Announces Successful Final Results of NicVAX(r) Immunogenicity Study," News Release, www.nabi.com, Oct. 29, 2008 (accessed Nov. 8, 2010).

Hatsukami et al., "Nicotine Vaccine: Results of a Phase 2, Multi-Center Study," PowerPoint presentation, 2005 (17 pages).

Hatsukami et al., "Nicotine Vaccine: Results of a Phase 2, Multi-Center Study," PowerPoint presentation, 2005 (22 pages).

Nabi Biopharmaceuticals, "Form 8-K, Report of unscheduled material events or corporate changes," filed Nov. 7, 2007.

Nabi Biopharmaceuticals, "Form 8-K, Report of unscheduled material events or corporate changes," filed Dec. 14, 2007.

International Search Report issued on Feb. 6, 2012 in application No. PCT/US2011/061229.

* cited by examiner

| NicVAX | 6-Month 20-Week CAR | 9-Month 34-Week CAR | 12-Month 44-Week CAR |
|---|---|---|---|
| Schedule 2 400 µg | 18% (n=9/51) p=0.015 | 18% (n=9/51) p=0.016 | 16% (n=8/51) p=0.038 |
| Schedule 2 200 µg | 14% (n=7/50) p=0.054 | 14% (n=7/50) p=0.053 | 14% (n=7/50) p=0.056 |
| Schedule 1 400 µg | 6% (n=3/50) p=0.87 | 6% (n=3/50) p=0.92 | 6% (n=3/50) p=0.96 |
| Schedule 1 200 µg | 8% (n=4/50) p=0.84 | 6% (n=3/50) p=0.88 | 6% (n=3/50) p=0.88 |
| Placebo | 6% (6/100) | 6% (6/100) | 6% (6/100) |

Figure 3

| | Continuous Abstinence | | |
|---|---|---|---|
| | 6-Month (Wk 19-26) | 12-Month (Wk 19-52) | 12-Month 44-Week |
| NicVAX High Antibody | 25% (n=15/61)<br>p=0.02<br>OR=2.69 (1.14–6.37) | 20% (n=12/61)<br>p=0.04<br>OR=2.64 (1.03–6.79) | 18% (n=11/61)<br>p=0.01<br>OR= 3.84 (1.32–11.20) |
| NicVAX Low Antibody | 9% (n=13/140)<br>p=0.46<br>OR=0.73 (0.31–1.71) | 7% (n=10/140)<br>p=0.43<br>OR=0.68 (0.26–1.76) | 7% (n=10/140)<br>p=0.67<br>OR=1.26 (0.43–3.65) |

Figure 4A

SMOKING CESSATION KIT AND METHOD

RELATED APPLICATIONS

This application claims the benefit of priority under 35 U.S.C. §119(e) to U.S. provisional application 61/129,247, filed Jun. 13, 2008, the entire contents of which are incorporated herein by reference.

GOVERNMENT RIGHTS IN THE INVENTION

The inventions disclosed herein were partly funded by grants. Therefore, to the extent that rights to such inventions may accrue to the U.S. government, the following statement, required under 37 C.F.R. §401.14(f)(4) applies: This invention was made with government support under Grant No. 5R01DA17894-2 awarded by the National Institute on Drug Abuse. The government has certain rights in the invention.

FIELD OF THE INVENTION

The present invention relates to the field of smoking cessation and provides methods, devices and kits for smoking cessation.

BACKGROUND

Smoking is a global healthcare problem. The World Health Organization estimates that there are 1.3 billion smokers worldwide today and nearly five million tobacco-related deaths each year. If current smoking patterns continue, smoking will cause some 10 million deaths each year by 2020. According to the U.S. Center for Disease Control (CDC), tobacco use is the single leading preventable cause of death in the U.S., responsible for approximately 438,000 deaths each year. In addition, it is estimated that smoking results in an annual health-related economic cost of approximately $157 billion. The CDC estimates that, among the 45 million adult smokers in the U.S., 70% want to quit, but less than five percent of those who try to quit remain smoke-free after 12 months.

One reason it is difficult to quit smoking is addiction to the nicotine in cigarettes and other tobacco products. Nicotine is a small molecule that upon inhalation into the body quickly passes into the bloodstream and subsequently reaches the brain by crossing the blood-brain barrier. Once in the brain, the nicotine binds to nicotinic receptors, which results in the release of stimulants, such as dopamine, providing the smoker with a positive sensation, which leads to addiction.

There remains a need, therefore, for methods, devices and kits for smoking cessation.

SUMMARY

In one embodiment, the invention provides a kit for determining whether it is an advantageous time for a subject to quit smoking, comprising:
  (a) an agent that specifically binds anti-nicotine antibodies;
  (b) instructions to use the agent to measure the level of anti-nicotine antibodies in serum from said subject; and
  (c) instructions indicating that serum anti-nicotine antibody levels of at least a first specified threshold level indicates that it is an advantageous time for the subject to quit smoking and/or that serum anti-nicotine antibody levels below the first specified threshold level do not indicate that it is an advantageous time for the subject to quit smoking.

In some embodiments, the first specified threshold level is selected from the group consisting of at least about 6 µg/ml, at least about 10 µg/ml, at least about 12 µg/ml, at least about 15 µg/ml, at least about 20 µg/ml, and at least about 25 µg/ml.

In other embodiments, the first specified threshold level is selected from the group consisting of up to at least about 25 µg/ml, at least about 30 µg/ml, at least about 35 µg/ml, at least about 40 µg/ml, at least about 45 µg/ml, and at least about 50 µg/ml.

In other embodiments, the first specified threshold level is directly correlated with the number of doses of a nicotine immunogenic composition that the subject has received prior to the measuring of the level of anti-nicotine antibodies. For instance, the first specified threshold anti-nicotine antibody level can be selected from at least 25 µg/ml for up to two prior doses, at least 50 µg/ml for three prior doses, at least 75 µg/ml for four prior doses, and at least 100 µg/ml for five prior doses.

In other embodiments, the first specified threshold level is directly correlated with the subject's degree of addiction to nicotine as measured by at least one of the following factors:
  (i) the degree of addiction, as measured by the baseline smoking level;
  (ii) the degree of addiction, as measured by the number of cigarettes smoked immediately prior to the measurement of anti-nicotine antibodies;
  (iii) the degree of addiction, as measured by a questionnaire;
  (iv) the number of previous quit attempts made within a certain period of time;
  (v) the total number of years smoked;
  (vi) the total number of continuous years smoked; and
  (vii) how soon in the morning after awakening on a given day the subject craves or actually lights the first cigarette or consumes other form(s) of nicotine.

In still other embodiments, the first specified threshold level is inversely correlated with the amount of counseling the subject receives.

In other embodiments, the first specified threshold level is correlated with the subject's number of cigarettes smoked per day. For instance, the first specified threshold level can be selected from the group consisting of at least about 25 µg/ml, at least about 30 µg/ml, at least about 35 µg/ml, at least about 40 µg/ml, at least about 45 µg/ml, and at least about 50 µg/ml, for subjects with a number of cigarettes smoked per day of 30 or greater, or is from about 1.5 to about 2.0 times the subject's number of cigarettes smoked per day.

In still other embodiments, the agent comprises nicotine or a nicotine derivative. For example, the agent can comprise 3'aminomethylnicotine.

In some embodiments, the kit comprises an anti-nicotine antibody standard solution containing anti-nicotine antibodies.

In other embodiments, the kit comprises instructions indicating that a nicotine immunogenic composition should be administered to the subject if the subject's serum anti-nicotine antibody levels are not at or above a second specified threshold level. For example, the second specified threshold level can be selected from the group consisting of at least about 6 µg/ml, at least about 10 µg/ml, at least about 12 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, and at least about 50 µg/ml, or is from about 1.5 to about 2.0 times the subject's number of cigarettes smoked per day.

In some embodiments, the agent that specifically binds anti-nicotine antibodies is provided in an analytical test device that measures the level of anti-nicotine antibodies in the serum and produces a signal that is correlated with the measured level of anti-nicotine antibodies in the serum. Thus, for instance, the analytical test device can include a device by which a user can input data related to at least one of the following factors: the number of doses of a nicotine immunogenic composition that the subject has received prior to the measuring of the level of anti-nicotine antibodies; the subject's degree of addiction to nicotine, and the amount of counseling the subject receives.

In some embodiments of the kit, the analytical test device includes a device by which a user can input the subject's number of cigarettes smoked per day, and wherein the signal indicates whether the measured level of anti-nicotine antibodies is at least a threshold antibody level correlated with the subject's number of cigarettes smoked per day.

In other embodiments, the kit comprises a nicotine immunogenic composition. In exemplary embodiments of the kit, the nicotine immunogenic composition comprises a nicotine-carrier conjugate comprising 3'aminomethylnicotine.

The invention also provides for a method for determining an advantageous time for a subject to quit smoking, comprising:
  (a) measuring the level of anti-nicotine antibodies in serum from said subject; and
  (b) correlating a first specified threshold serum anti-nicotine antibody level with an advantageous time for the subject to quit smoking.

In some embodiments, the first specified threshold level is directly correlated with the subject's degree of addiction to nicotine as measured by at least one of the following factors:
  (i) the degree of addiction, as measured by the baseline smoking level;
  (ii) the degree of addiction, as measured by the number of cigarettes smoked immediately prior to the measurement of anti-nicotine antibodies;
  (iii) the degree of addiction, as measured by a questionnaire;
  (iv) the number of previous quit attempts made within a certain period of time;
  (v) the total number of years smoked;
  (vi) the total number of continuous years smoked; and
  (vii) how soon in the morning after awakening on a given day the subject craves or actually lights the first cigarette or consumes other form(s) of nicotine.

In some embodiments, the first specified threshold level is inversely correlated with the amount of counseling the subject receives.

In other embodiments, the method further comprises, prior to step (b), determining at least one factor selected from the group consisting of a factor associated with the subject's degree of addiction to nicotine, the amount of counseling the subject receives, and the number of doses of a nicotine immunogenic composition that the subject has received.

In other embodiments, the method further comprises, prior to step (b), determining the subject's number of cigarettes smoked per day.

In other embodiments of the method, the first specified threshold level is correlated with the subject's number of cigarettes smoked per day, as outlined above.

In still other embodiments, first specified threshold level is directly correlated with the number of doses of a nicotine immunogenic composition that the subject has received prior to the measuring of the level of anti-nicotine antibodies.

Other embodiments provide for counseling the subject to have administered a nicotine immunogenic composition, if the subject's serum anti-nicotine antibody levels are not at or above a second specified threshold level.

In other embodiments, the method further comprises administering to the subject a nicotine immunogenic composition, if the subject's serum anti-nicotine antibody levels are not at or above a second specified threshold level. For example, the nicotine immunogenic composition can comprise a nicotine-carrier conjugate comprising 3'aminomethylnicotine.

In some embodiments, the method further comprises, prior to step (a), administering to the subject a nicotine immunogenic composition. For instance, the nicotine immunogenic composition can comprise a nicotine-carrier conjugate comprising 3'aminomethylnicotine.

The invention further provides for a method for counseling a subject on whether it is an advantageous time for the subject to quit smoking, comprising
  (a) measuring the level of anti-nicotine antibodies in serum from the subject; and
  (b) counseling the subject that it is an advantageous time to quit smoking if the subject's serum anti-nicotine antibody levels are at or above a first specified threshold level and/or that it is not an advantageous time to quit smoking if the subject's serum anti-nicotine antibody levels are below a first specified threshold level.

In addition, the invention provides for a kit for extending the duration of smoking abstinence in a subject who has quit smoking, comprising:
  (a) an agent that specifically binds anti-nicotine antibodies;
  (b) instructions to use the agent to measure the level of anti-nicotine antibodies in serum from the subject;
  (c) instructions indicating that a serum anti-nicotine antibody level less than a minimum level indicates that the subject should be administered a nicotine immunogenic composition, and/or instructions indicating that a serum anti-nicotine antibody level at or above the minimum level indicates that the subject should not be administered a nicotine immunogenic composition.

In some embodiments of the kit, the minimum threshold is one selected from at least 5 µg/mL, at least 10 µg/mL, at least 15 µg/mL, at least 20 µg/mL, at least 25 µg/mL, at least 35 µg/mL, and at least at least 45 µg/mL.

In other embodiments, the kit includes instructions to measure the level of anti-nicotine antibodies in serum from the subject at a time selected from the group consisting of at least 1 month, at least 2 months, at least 3 months, at least 4 months, at least 6 months, at least 9 months, at least 12 months, at least 18 months and at least 24 months after the subject has quit smoking.

In some embodiments, the minimum level is directly correlated with the subject's degree of addiction to nicotine as measured by at least one of the following factors
  (i) the degree of addiction, as measured by the baseline smoking level;
  (ii) the degree of addiction, as measured by the number of cigarettes smoked immediately prior to the measurement of anti-nicotine antibodies;
  (iii) the degree of addiction, as measured by a questionnaire;
  (iv) the number of previous quit attempts made within a certain period of time;
  (v) the total number of years smoked;
  (vi) the total number of continuous years smoked; and
  (vii) how soon in the morning after awakening on a given day the subject craves or actually lights the first cigarette or consumes other form(s) of nicotine.

In other embodiments, the minimum level is inversely correlated with the amount of counseling the subject receives.

In still other embodiments, the minimum level is directly correlated with the number of doses of a nicotine immunogenic composition that the subject has received prior to the measuring of the level of anti-nicotine antibodies.

In some embodiments of the kit, the kit further comprises a nicotine immunogenic composition. For instance, the nicotine immunogenic composition comprises a nicotine-carrier conjugate comprising 3'aminomethylnicotine.

The invention also provides a method for extending the duration of smoking abstinence in a subject who has quit smoking. comprising:

(a) determining whether the level of anti-nicotine antibodies in serum from the subject is less than a minimum level; and (b) administering to the subject a nicotine immunogenic composition if the subject's serum anti-nicotine antibody levels are not at or above the minimum level.

In some embodiments, the subject's serum anti-nicotine antibody level is measured at a time selected from the group consisting of at least 1 month, at least 2 months, at least 3 months, at least 4 months, at least 6 months, at least 9 months, at least 12 months, at least 18 months and at least 24 months after the subject has quit smoking.

In other embodiments, the minimum threshold level is directly correlated with the subject's degree of addiction to nicotine as measured by at least one of the following factors
  (i) the degree of addiction, as measured by the baseline smoking level;
  (ii) the degree of addiction, as measured by the number of cigarettes smoked immediately prior to the measurement of anti-nicotine antibodies;
  (iii) the degree of addiction, as measured by a questionnaire;
  (iv) the number of previous quit attempts made within a certain period of time;
  (v) the total number of years smoked;
  (vi) the total number of continuous years smoked; and
  (vii) how soon in the morning after awakening on a given day the subject craves or actually lights the first cigarette or consumes other form(s) of nicotine.

In still other embodiments, the minimum level is inversely correlated with the amount of counseling the subject receives.

Alternatively, in other embodiments, the minimum level is directly correlated with the number of doses of a nicotine immunogenic composition that the subject has received prior to the measuring of the level of anti-nicotine antibodies.

Some embodiments further provide for administering to the subject a nicotine immunogenic composition. For instance, the nicotine immunogenic composition comprises a nicotine-carrier conjugate comprising 3'aminomethylnicotine.

The invention also provides for a method for determining whether it is an advantageous time for a subject to quit smoking, comprising:

(a) measuring the level of anti-nicotine antibodies in serum from said subject; and (b) determining that it is an advantageous time for a subject to quit smoking if the measured level is at or above a first specified threshold serum anti-nicotine antibody level or that it is not an advantageous time for a subject to quit smoking if the measured level is below the first specified threshold serum anti-nicotine antibody level.

In some embodiments, the method further comprises, prior to step (b): (a') transforming data related to at least one factor selected from the group consisting of the subject's degree of nicotine addition, the level of counseling the subject receives, and the number of doses of a nicotine immunogenic composition the subject has received, into said first specified threshold serum anti-nicotine antibody level. For example, in some embodiments, step (a') comprises the use of written material (electronic or printed), a machine or a computer. The machine or computer can include a mechanical or electronic device for receiving the measured level of anti-nicotine antibodies in serum from said subject.

Alternatively, in other embodiments, the machine or computer includes a mechanical or electronic device for receiving data related to at least one factor selected from the group consisting of the subject's degree of nicotine addition, the level of counseling the subject receives, and the number of doses of a nicotine immunogenic composition the subject has received.

In still other embodiments, the machine or computer includes a mechanical or electronic device for outputting the first specified threshold serum anti-nicotine antibody level.

In yet other embodiments, the machine or computer produces a signal indicating that the measured level is at least the threshold antibody level and/or a signal indicating that the measured level is less than the threshold antibody level.

In some embodiments of the method, the written material correlates at least one factor selected from the group consisting of the subject's degree of nicotine addition, the level of counseling the subject receives, and the number of doses of a nicotine immunogenic composition the subject has received, with the first specified threshold serum anti-nicotine antibody level.

In other embodiments of the method, step (b) comprises the use of written material (electronic or printed), a machine or a computer.

The invention further provides for a method for determining whether it is an advantageous time for a subject to quit smoking, comprising:

(a) measuring the level of anti-nicotine antibodies in serum from said subject; and (b) determining that it is an advantageous time for a subject to quit smoking if the measured level is (i) at or above a first specified threshold serum anti-nicotine antibody level that indicates an advantageous time to quit smoking or (ii) that it is not an advantageous time for a subject to quit smoking if the measured level is below the first specified threshold serum anti-nicotine antibody level.

In addition, the invention provides for a method for determining a specified threshold serum or saliva anti-nicotine antibody level, comprising transforming data related to at least one factor selected from the group consisting of the subject's degree of nicotine addiction, the level of counseling the subject receives, and the number of doses of a nicotine immunogenic composition the subject has received, into a first specified threshold serum anti-nicotine antibody level.

In some embodiment, the transforming occurs by an electronic processing circuit.

The invention also provides for device for determining a specified threshold serum or saliva anti-nicotine antibody level, the device comprising:

a user interface configured to receive at least one user input, the input indicative of at least one of a subject's degree of nicotine addiction, the level of counseling the subject receives, and the number of doses of a nicotine immunogenic composition the subject has received;

an electronic processing circuit configured to calculate a first specified threshold serum or saliva anti-nicotine antibody level based on the at least one user input; and an output device configured to provide an output signal indicative of the first specified threshold serum or saliva anti-nicotine antibody level.

Also, the invention provides for a device for determining whether it is an advantageous time for a subject to quit smoking, the device comprising:

a sensor configured to contact a biological sample from the subject containing a level of anti-nicotine antibodies, the sensor configured to provide a sensor output signal based upon the level of anti-nicotine antibodies in the biological sample;

a processing circuit communicably coupled to the sensor, the processing circuit configured to determine the level of anti-nicotine antibodies present in the biological sample based on the sensor output signal; and an output device configured to generate an output based upon the determined level of anti-nicotine antibodies present in the biological sample.

For instance, in some embodiments, the processing circuit is further configured to compare the determined level of anti-nicotine antibodies present in the biological sample to a first specified threshold anti-nicotine antibody level, and wherein the output device is further configured to generate at least one of (i) a first output, if the determined level of anti-nicotine antibodies is at or above a first specified threshold anti-nicotine antibody level, to indicate that it is an advantageous time for a subject to quit smoking and (ii) a second output, if the determined level of anti-nicotine antibodies is below a first specified threshold anti-nicotine antibody level to indicate that it is not an advantageous time for a subject to quit smoking.

In still other embodiments, the device further comprises a user interface configured to receive at least one user input indicative of at least one factor selected from the group consisting of the subject's degree of nicotine addition, the level of counseling the subject receives, and the number of doses of a nicotine immunogenic composition the subject has received, and wherein, the first specified threshold serum or saliva anti-nicotine antibody level is based on the at least one user input.

Other embodiments of the device provide for the processing circuit to be further configured to compare the determined level of anti-nicotine antibodies present in the biological sample to a specified second threshold serum anti-nicotine antibody level, and wherein the output device is further configured to generate at least one of (i) a third output, if the determined level of anti-nicotine antibodies is not at or above the second specified threshold serum anti-nicotine antibody level, to indicate that it is an advantageous time for the subject to be administered a subsequent dose of a nicotine immunogenic composition and (ii) a fourth output, if the determined level of anti-nicotine antibodies is above the second specified threshold serum anti-nicotine antibody level, to indicate that it is not an advantageous time for the subject to be administered a subsequent dose of a nicotine immunogenic composition.

The invention also provides for a device for determining whether it is an advantageous time for a subject to quit smoking, the device comprising:

a sensing element configured to contact a biological sample from the subject, the sensing element configured to generate an output signal indicative of the level of anti-nicotine antibodies in the biological sample; and an output element responsive to the output signal generated by the sensing element, the output element configured to generate at least one of (i) a first output, if the determined level of anti-nicotine antibodies is at or above a first specified threshold anti-nicotine antibody level, to indicate that it is an advantageous time for the subject to quit smoking and (ii) a second output, if the determined level of anti-nicotine antibodies is below a first specified threshold serum anti-nicotine antibody level, to indicate that it is not an advantageous time for the subject to quit smoking.

In some embodiments of the device, the output element is further configured to generate at least one of (i) a third output, if the determined level of anti-nicotine antibodies is not at or above a second specified threshold serum anti-nicotine antibody level, to indicate that it is an advantageous time for the subject to be administered a subsequent dose of a nicotine immunogenic composition and (ii) a fourth output, if the determined level of anti-nicotine antibodies is above the second specified threshold serum anti-nicotine antibody level, to indicate that it is not an advantageous time for the subject to be administered a subsequent dose of a nicotine immunogenic composition.

The invention also provides for a device for determining whether it is an advantageous time for a subject who has been administered a dose of a nicotine immunogenic composition to be administered a subsequent dose of a nicotine immunogenic composition, the device comprising:

a sensor configured to contact a biological sample from the subject containing a level of anti-nicotine antibodies, the sensor configured to provide a sensor output signal based upon the level of anti-nicotine antibodies in the biological sample;

a processing circuit communicably coupled to the sensor, the processing circuit configured to determine the level of anti-nicotine antibodies present in the biological sample based on the sensor output signal and to compare the determined level of anti-nicotine antibodies present in the biological sample to a specified second threshold serum anti-nicotine antibody level; and an output device configured to generate at least one of (i) a first output, if the determined level of anti-nicotine antibodies is not at or above the second specified threshold serum anti-nicotine antibody level, to indicate that it is an advantageous time for the subject to be administered a subsequent dose of a nicotine immunogenic composition and (ii) a second output, if the determined level of anti-nicotine antibodies is above the second specified threshold serum anti-nicotine antibody level, to indicate that it is not an advantageous time for the subject to be administered a subsequent dose of a nicotine immunogenic composition.

The invention also provides for a device for determining whether it is an advantageous time for a subject who has been administered a dose of a nicotine immunogenic composition to be administered a subsequent dose of a nicotine immunogenic composition, the device comprising:

a sensing element configured to contact a biological sample from the subject, the sensing element configured to generate an output signal indicative of the level of anti-nicotine antibodies in the biological sample; and an output element responsive to the output signal generated by the sensing element, the output element configured to generate at least one of (i) a first output, if the determined level of anti-nicotine antibodies is not at or above a second specified threshold serum anti-nicotine antibody level, to indicate that it is an advantageous time for the subject to be administered a subsequent dose of a nicotine immunogenic composition and (ii) a second output, if the determined level of anti-nicotine antibodies is above the second specified threshold serum anti-nicotine antibody level, to indicate that it is not an advantageous time for the subject to be administered a subsequent dose of a nicotine immunogenic composition.

Further, the invention provides for a device for increasing the duration of smoking abstinence in a subject who has quit smoking, the device comprising:

a sensor configured to contact a biological sample from the subject containing a level of anti-nicotine antibodies, the sensor configured to provide a sensor output signal based upon the level of anti-nicotine antibodies in the biological sample;

a processing circuit communicably coupled to the sensor, the processing circuit configured to determine the level of anti-nicotine antibodies present in the biological sample based on the sensor output signal and to compare the determined level of anti-nicotine antibodies present in the biological sample to a minimum level; and an output device configured to generate at least one of (i) a first output, if the determined level of anti-nicotine antibodies is not at or above the minimum level, to indicate that it is an advantageous time for the subject to be administered a dose of a nicotine immunogenic composition and (ii) a second output, if the determined level of anti-nicotine antibodies is above the minimum level, to indicate that it is not an advantageous time for the subject to be administered a dose of a nicotine immunogenic composition.

The invention provides for a device for increasing the duration of smoking abstinence in a subject who has quit smoking, the device comprising:

a sensing element configured to contact a biological sample from the subject, the sensing element configured to generate an output signal indicative of the level of anti-nicotine antibodies in the biological sample; and an output element responsive to the output signal generated by the sensing element, the output element configured to generate at least one of (i) a first output, if the determined level of anti-nicotine antibodies is not at or above a minimum level, to indicate that it is an advantageous time for the subject to be administered a dose of a nicotine immunogenic composition and (ii) a second output, if the determined level of anti-nicotine antibodies is above the minimum level, to indicate that it is not an advantageous time to for the subject to be administered a dose of a nicotine immunogenic composition.

In some embodiments, the device described herein further comprises a body to support the sensing element and the output element, the body having a handle portion located at an end of the body generally opposite of the sensing element to allow a user to conveniently place the sensing element into contact with the biological sample.

In other embodiments, the sensing element includes a chemical that generates an output signal responsive to the level of anti-nicotine antibodies in the biological sample and the output element is a chemical that changes color in response to the output signal of the sensing element.

In some embodiments of the device described herein, the first specified threshold level is selected from the group consisting of at least about 6 µg/ml, at least about 10 µg/ml, at least about 12 µg/ml, at least about 15 µg/ml, at least about 20 µg/ml, and at least about 25 µg/ml.

In other embodiments, the first specified threshold level is directly correlated with the number of doses of a nicotine immunogenic composition that the subject has received prior to the measuring of the level of anti-nicotine antibodies. For instance, the first specified threshold anti-nicotine antibody level is selected from at least 25 µg/ml for up to two prior doses, at least 50 µg/ml for three prior doses, at least 75 µg/ml for four prior doses, and at least 100 µg/ml for five prior doses.

In still other embodiments of the device herein described, the first specified threshold level is directly correlated with the subject's degree of addiction to nicotine as measured by at least one of the following factors:

(i) the degree of addiction, as measured by the baseline smoking level;
(ii) the degree of addiction, as measured by the number of cigarettes smoked immediately prior to the measurement of anti-nicotine antibodies;
(iii) the degree of addiction, as measured by a questionnaire;
(iv) the number of previous quit attempts made within a certain period of time;
(v) the total number of years smoked;
(vi) the total number of continuous years smoked; and
(vii) how soon in the morning after awakening on a given day the subject craves or actually lights the first cigarette or consumes other form(s) of nicotine.

In other embodiments, the first specified threshold level is inversely correlated with the amount of counseling the subject receives.

Alternatively, the first specified threshold level is correlated with the subject's number of cigarettes smoked per day. For example, in some embodiments, the first specified threshold level is selected from the group consisting of at least about 25 µg/ml, at least about 30 µg/ml, at least about 35 µg/ml, at least about 40 µg/ml, at least about 45 µg/ml, and at least about 50 µg/ml, for subjects with a number of cigarettes smoked per day of 30 or greater, or is from about 1.5 to about 2.0 times the subject's number of cigarettes smoked per day.

In still other embodiments of the device, the first specified threshold level is selected from the group consisting of up to at least about 25 µg/ml, at least about 30 µg/ml, at least about 35 µg/ml, at least about 40 µg/ml, at least about 45 µg/ml, and at least about 50 µg/ml.

In some embodiments of the device described herein, the second specified threshold level is selected from the group consisting of at least about 6 µg/ml, at least about 10 µg/ml, at least about 12 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, and at least about 50 µg/ml, or is from about 1.5 to about 2.0 times the subject's number of cigarettes smoked per day.

In some embodiments of the device that provide for a nicotine immunogenic composition, the nicotine immunogenic composition comprises a nicotine-carrier conjugate comprising 3'aminomethylnicotine.

In other embodiments of the device herein described, the minimum level is one selected from at least 5 µg/mL, at least 10 µg/mL, at least 15 µg/mL, at least 20 µg/mL, at least 25 µg/mL, at least 35 µg/mL, and at least at least 45 µg/mL.

Alternatively, the minimum level is directly correlated with the subject's degree of addiction to nicotine as measured by at least one of the following factors (i) the degree of addiction, as measured by the baseline smoking level;
(ii) the degree of addiction, as measured by the number of cigarettes smoked immediately prior to the measurement of anti-nicotine antibodies;
(iii) the degree of addiction, as measured by a questionnaire;
(iv) the number of previous quit attempts made within a certain period of time;
(v) the total number of years smoked;
(vi) the total number of continuous years smoked; and
(vii) how soon in the morning after awakening on a given day the subject craves or actually lights the first cigarette or consumes other form(s) of nicotine.

In some embodiments, the minimum level is inversely correlated with the amount of counseling the subject receives.

Alternatively, the minimum level is directly correlated with the number of doses of a nicotine immunogenic composition that the subject has received prior to the measuring of the level of anti-nicotine antibodies.

The invention additionally provides in some embodiments a use of an agent that specifically binds anti-nicotine antibodies in a method of determining whether it is an advantageous time for a subject to quit smoking.

In other embodiments, the invention provides for the use of an agent that specifically binds anti-nicotine antibodies for the preparation of a diagnostic composition for determining whether it is an advantageous time for a subject to quit smoking.

In another embodiment, the invention provides for an agent that specifically binds anti-nicotine antibodies for use in a method of determining whether it is an advantageous time for a subject to quit smoking.

In still another embodiment, the invention provides for the use of an immunogenic composition in a method of determining whether it is an advantageous time for a subject to quit smoking.

In other embodiments the invention provides for the use of immunogenic composition for the preparation of a diagnostic composition for determining whether it is an advantageous time for a subject to quit smoking.

In yet another embodiment, the invention provides for an immunogenic composition for use in a method of determining whether it is an advantageous time for a subject to quit smoking.

The invention provides in still another embodiment the use of an immunogenic composition in a method of counseling a subject whether it is an advantageous time for a subject to quit smoking.

In another embodiment, the invention provides for the use of an immunogenic composition for the preparation of a diagnostic composition for counseling a subject on whether it is an advantageous time for a subject to quit smoking.

In another embodiment, the invention provides for an immunogenic composition for use in a method of counseling a subject on whether it is an advantageous time for a subject to quit smoking.

In still another embodiment, the invention provides for the use of an agent that specifically binds anti-nicotine antibodies in a method of extending the duration of smoking cessation in a subject who has quit smoking.

In another embodiment, the invention provides for the use of an agent that specifically binds anti-nicotine antibodies for the preparation of a diagnostic composition for extending the duration of smoking cessation in a subject who has quit smoking.

In another embodiment, the invention provides for an agent that specifically binds anti-nicotine antibodies for use in a method of extending the duration of smoking cessation in a subject who has quit smoking.

In another embodiment, the invention provides for the use of a nicotine immunogenic composition in a method for extending the duration of smoking cessation in a subject who has quit smoking, wherein the composition is administered to the subject when subject's serum anti-nicotine antibody levels are not at or above a predefined minimum level.

In another embodiment, the invention provides for the use of a nicotine immunogenic composition for the preparation of a pharmaceutical composition for extending the duration of smoking cessation in a subject who has quit smoking, wherein the preparation is administered to the subject when subject's serum anti-nicotine antibody levels are not at or above a predefined minimum level.

In another embodiment, the invention provides for a nicotine immunogenic composition for use in a method for extending the duration of smoking cessation or abstinence in a subject who has quit smoking, wherein the composition is administered to the subject when subject's serum anti-nicotine antibody levels are not at or above a predefined minimum level.

BRIEF DESCRIPTION OF THE DRAWINGS

FIG. 3 shows the numbers and percentages of subjects who achieved total abstinence ("Continuous Abstinence Rate") by the 6 month, 9 month and 12 month time points by dose group.

FIG. 4A shows the numbers and percentages of twelve-month continuous abstinence (smoking cessation) based on treatment group and subject serum antibody levels (high versus low serum antibody levels).

DETAILED DESCRIPTION

Figure 1:
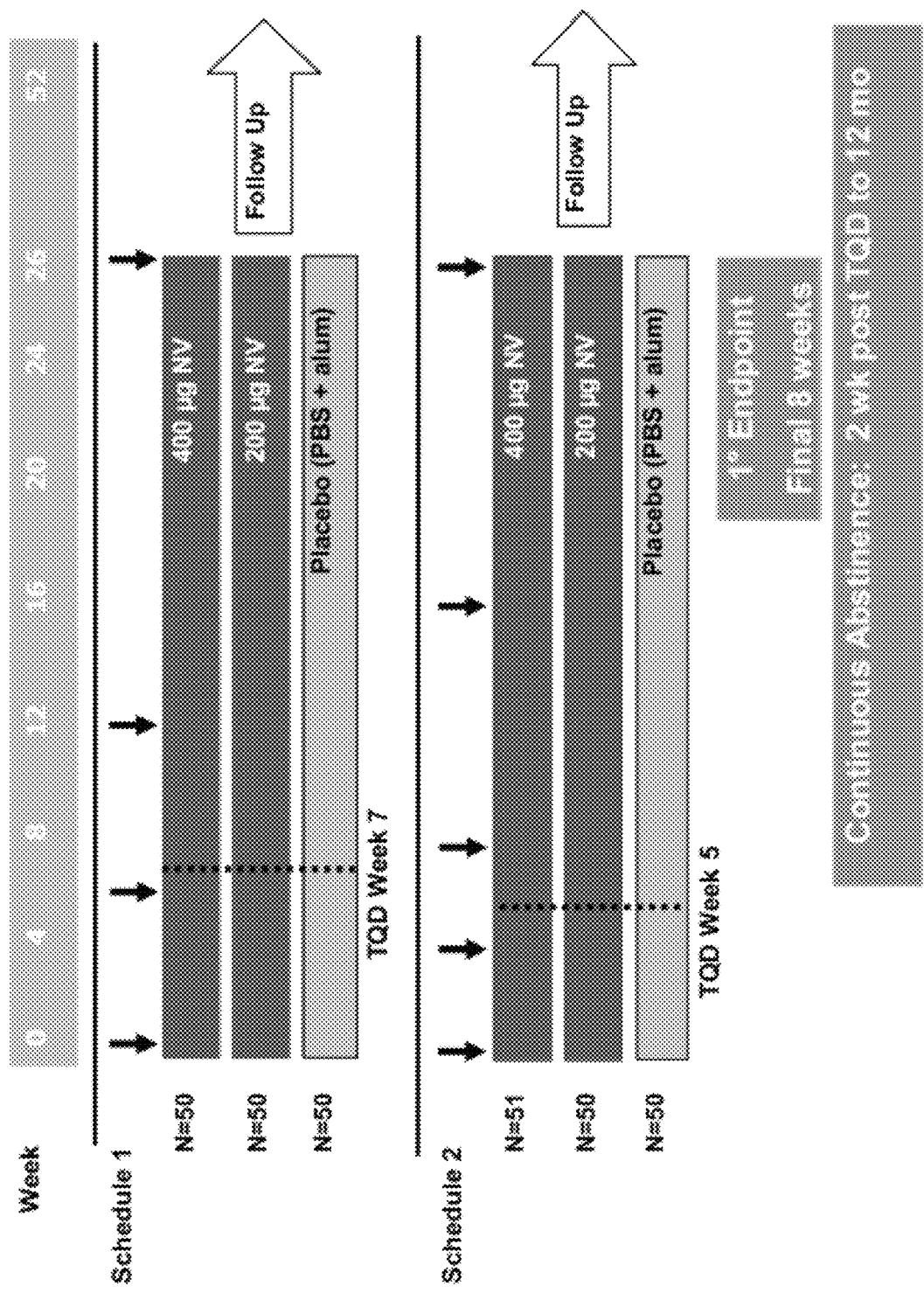
FIG. 1 shows the design for the randomized, double-blind, and placebo-controlled clinical Phase IIb study described in the Examples.

Nicotine vaccines have been disclosed in the art as smoking cessation aids. Typically such vaccines include a nicotine-carrier conjugate that is administered to induce anti-nicotine antibodies. A "nicotine-carrier conjugate" designates a compound that comprises nicotine (or a nicotine derivative) covalently linked to a second molecule, or carrier. Such a linkage may be direct or via a linker or linking moiety. Examples of such conjugates, and methods for their preparation, are well known in the art. See, for example, U.S. Pat. No. 6,232,082 (Ennifar), U.S. App. 2007/0129551 A1 (Ennifar), U.S. Pat. No. 5,876,727 (Swain) and U.S. Pat. No. 6,932,971 (Bachmann) (describing nicotine-virus like particle conjugates). The general theory behind nicotine vaccines is that they induce nicotine-specific antibodies that bind nicotine and reduces its distribution to the brain, blocking nicotine drug effects, including those responsible for nicotine addiction. See, e.g., Hatsukani et al., Clin. Pharm. & Ther. 78: 456-67 (2005).

The present inventors have discovered that a subject's antibody levels of anti-nicotine antibodies (such as serum antibody levels or levels of secreted antibodies, such as mucosal antibody levels, including antibody levels measured in saliva) can be used to determine an advantageous time to quit smoking, to determine whether it is an advantageous time to quit, and/or to maintain (or extend the duration of) smoking abstinence, such that the subject has a greater chance of successfully quitting smoking and achieving long-term abstinence. The invention is useful for instance, as an aid to smoking cessation and long-term abstinence.

Thus, for example, in accordance with the methods, devices and kits described herein, subjects who have been treated with a vaccine to induce anti-nicotine antibodies, such as a vaccine comprising a nicotine-carrier conjugate, can be counseled on an advantageous time to quit smoking, and/or can be counseled on whether or when a dose of vaccine should be administered to achieve an advantageous time to quit smoking and/or extend the duration of abstinence.

Technical and scientific terms used herein have the meanings commonly understood by one of ordinary skill in the art to which the present invention pertains, unless otherwise defined. Reference is made herein to various methodologies known to those of ordinary skill in the art. Any suitable materials and/or methods known to those of ordinary skill in the art can be utilized in carrying out the present invention. However, specific materials and methods are described.

As used herein, the singular forms "a," "an," and "the" designate both the singular and the plural, unless expressly stated to designate the singular only.

The term "about" and the use of ranges in general, whether or not qualified by the term about, means that the number comprehended is not limited to the exact number set forth herein, and is intended to refer to ranges substantially within the quoted range while not departing from the scope of the invention. As used herein, "about" will be understood by persons of ordinary skill in the art and will vary to some extent on the context in which it is used. If there are uses of the term which are not clear to persons of ordinary skill in the art given the context in which it is used, "about" will mean up to plus or minus 10% of the particular term.

In accordance with some embodiments, there are provided methods, devices and kits for determining an advantageous time to quit smoking, and for quitting smoking at an advantageous time. As used in this application, "an advantageous time to quit smoking" is a time when a subject has at least a 20% chance of abstaining from smoking for at least four weeks. Four weeks is a generally accepted time period for measuring smoking cessation. Thus, in some embodiments, the methods, devices and kits described herein will determine a time to quit smoking such that the subject has at least a 20% chance of abstaining from smoking for at least four weeks. In some embodiments, the subject will have at least a 25% chance, at least a 30% chance, at least a 35% chance, at least a 40% chance, at least a 45% chance, at least a 50% chance, or greater, of abstaining from smoking for at least four weeks.

In some embodiments, the methods, devices and kits described herein will determine a time to quit smoking such that the subject will have at least a 15% chance of abstaining from smoking for at least 4 months, including at least a 20% chance, at least a 25% chance, at least a 30% chance, at least a 35% chance, or greater, of abstaining from smoking for at least 4 months. Four months is an accepted time period for measuring long-term smoking abstinence.

In some embodiments, the methods, devices and kits described herein will determine a time to quit smoking such that the subject will have at least a 10% chance of abstaining from smoking for at least 12 months, including at least a 15% chance, at least a 20% chance, at least a 25% chance, or greater, of abstaining from smoking for at least 12 months. In some embodiments, the methods, devices and kits described herein will determine a time to quit smoking such that the subject has a significantly improved probability of abstaining from smoking for at least four weeks, at least 6 months, or at least 12 months, such as at least 1.25, 1.5, 1.75, 2, 2.5, 3, 3.5, or greater, times the probability of abstaining from smoking, as compared to a comparable subject in need of smoking cessation treatment who is not guided by the methods described herein.

As used herein a subject in need of smoking cessation treatment or in need of initiation of abstinence is a human subject who smokes cigarettes or other tobacco products or chews tobacco, or uses other nicotine products. Such a subject may or may not be physically addicted to nicotine and/or psychologically addicted to smoking cigarettes or using other tobacco or other nicotine products. Typical subjects in need of smoking cessation treatment smoke or use tobacco or other nicotine products daily, such as smoking at least 1 cigarette a day, or more, such as at least about 5, at least about 10, at least about 15, at least about 20, or more, cigarettes per day, including fewer than 10, 10-20, 20-30, 30-40, or 40 or more (or the equivalent use of other tobacco or nicotine products). Other nicotine products include, but are not limited to chewing tobacco, pipes, cigars, electronic cigarettes, and other nicotine delivery devices.

As used herein "serum" includes blood or plasma. In practicing the methods and using the kits and devices described herein, a sample of blood from the subject can be used to assess serum antibody levels. Additionally or alternatively, the methods, kits and devices described herein can be practiced using a sample of saliva from the subject to assess secreted antibody levels. For convenience, the invention is described below in terms of serum antibody levels, but it should be understood that each embodiment could be practiced with reference to secreted antibody levels. The practitioner can determine corresponding secreted antibody levels using routine methodologies.

As used in this application, an "agent that specifically binds anti-nicotine antibodies" means any compound that will specifically bind to an anti-nicotine antibody. Such agents include, but are not limited to nicotine and nicotine derivatives, such as 3'-aminomethylnicotine, 3'-hydroxymethylnicotine, 5-aminonicotine, 6-aminonicotine, nicotine substituted with a halogen (e.g., bromine) at the 5 or 6 position, and other nicotine derivatives, such as nicotine derivatized at the pyridine or pyrolidine ring. Such agents may be immobilized to matrices through conjugating or complexing to proteins such as BSA or any other protein serologically distinctive from and non-cross reactive with rEPA, polyglutamic acid, poly-amino acid or other means to facilitate its immobilization to matrices. Those skilled in the art of immunology readily understand what is meant by "specifically binds." For example, an agent "specifically binds" to anti-nicotine antibodies if it binds to anti-nicotine antibodies under conditions where it will not bind to another molecule, either generally or under the specific test conditions being used.

As noted above, the inventors have discovered that when serum or secreted anti-nicotine antibody levels reach a threshold level, the chance for a successful quit attempt is significantly increased. While not wanting to be bound by any theory, it is believed that the greater the serum or secreted anti-nicotine antibody level, the greater the chance of a successful quit attempt. Thus, in some embodiments, a serum anti-nicotine antibody level of at least about 6 µg/ml indicates an advantageous time to quit. In other embodiments, a serum anti-nicotine antibody level of at least about 10 µg/ml, at least about 12 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, or, at least about 50 µg/ml indicates an advantageous time to quit. Thus, for example, serum anti-nicotine antibody levels of at least 6 µg/ml, at least 10 µg/ml, at least 12 µg/ml, at least 15 µg/ml, at least 20 µg/ml, at least 25 µg/ml, at least 30 µg/ml, at least 35 µg/ml, at least 40 µg/ml, at least 45 µg/ml, or at least 50 µg/ml may indicate an advantageous time to quit smoking. In other embodiments, a serum anti-nicotine antibody level (in µg/ml) of from at least about 1.5 to at least about 2.0 times the number of cigarettes smoked per day by the subject indicates an advantageous time to quit. The practitioner can determine corresponding secreted antibody levels using routine methodologies.

Methods for measuring the level of anti-nicotine antibodies in a sample, such as a serum or saliva sample, are well known in the art. For example, an agent that specifically binds anti-nicotine antibodies can be used in various methods to detect the presence and level of anti-nicotine antibodies in a sample. One detection method is the so-called ELISA (Enzyme-Linked-Immunosorbent-Assay), which is well known in the art as a method for quantifying antibody level. As illustrated in the Examples, 3'-aminomethylnicotine conjugated to polyglutamic acid can be used in an ELISA to determine the level of anti-nicotine antibodies in human serum. Example 10 of U.S. Pat. No. 6,232,082 describes a similar ELISA for anti-nicotine antibodies. Example 2 of U.S. Pat. No. 6,932,971 describes an ELISA employing a nicotine-bovine serum albumin conjugate to detect anti-nicotine antibodies. Example 26 of U.S. Pat. No. 5,876,727 also describes an anti-nicotine antibody ELISA. These or similar methods can be used in the context of the present invention. Devices for conducting such assays are known in the art, such as devices for conducting colorometric assays, including dipstick-type devices.

Other methods for detecting and quantifying the level of anti-nicotine antibodies by binding to nicotine or its chemical derivatives can employ different detection methods, such as radioimmuno assay methods, spectroscopic methods, quantum dots, florescence, bioluminescence, chromatographic, mass spectrometry or other methods useful for detecting antibody/antigen interactions, including but not limited to those that measure changes in physical characteristics upon binding by the antibody (e.g. size, mobility, transport, diffusion, etc.). Indeed, any method useful for detecting and quantifying the level of anti-nicotine antibodies can be used.

Nicotine addiction is a multi-factorial, behavioral, social and chemical addiction; thus, the threshold antibody levels described herein may be seen as guidelines for moderate to heavy smokers who are willing and motivated to quit smoking. For example, the threshold antibody levels that pertain to the kits, devices and methods described herein can vary depending upon the degree to which an individual is addicted to or dependent upon nicotine and/or how many cigarettes or other sources of nicotine the individual consumes, with higher levels pertaining to subjects with a greater degree of addiction. The threshold antibody level required for a given subject to successfully quit smoking and/or achieve long-term abstinence also depends upon the willingness of the subject to quit/abstain and the amount of behavioral counseling the subject receives, such as by telephone, internet, and/or in person, with lower levels pertaining to a subject with a greater willingness to quit and/or receiving a greater amount of counseling.

Thus, in some embodiments, the threshold antibody levels are correlated with one or more of a variety of factors including but not limited to the subject's degree of addiction, the willingness of the subject to quit/abstain, and the amount of behavioral counseling the subject receives. For example, threshold antibody levels may be directly correlated with one or more of the following factors associated with nicotine addiction, such that, for example, a higher threshold antibody level would pertain for a subject with a greater degree of addiction:

(i) the degree of addiction, as measured by the baseline smoking level, such as the average number of cigarettes smoked per day;

(ii) the degree of addiction, as measured by the number of cigarettes smoked immediately prior to the measurement of anti-nicotine antibodies, such as the number of cigarettes smoked per day over the course of a few days to a week prior to the measurement of anti-nicotine antibodies as described herein;

(iii) the degree of addiction, as measured by one or more questionnaires, including any subscales, intended to discern the degree of nicotine addiction, such as by a Fagerstrom test (see K O Fagerstrom et al. *J. Behav. Med.* 12 (1989) 159-181; T F Heatherton et al. *Brit. J. Addict.* 86 (1991) 1119-1127)

(iv) the number of previous quit attempts made within a certain period of time, such as within one month, within three months, within six months, within one year, within three years or within five years;
(v) the total number of years smoked;
(vi) the total number of continuous years smoked; and
(vii) how soon in the morning after awakening on a given day the subject craves or actually lights the first cigarette or consumes other form(s) of nicotine.

Additionally or alternatively, threshold antibody levels may be inversely correlated with the amount of behavioral counseling the subject receives, such that, for example, a lower threshold antibody level may pertain for a subject receiving behavioral counseling.

In some embodiments, the threshold varies with the subject's number of cigarettes smoked per day, such as the number of cigarettes smoked the day before a target quit date (or a day within a few days, such as 1-3 days, before a target quit date), or the subject's average number of cigarettes smoked per day (for example as averaged over the week prior to the target quit date). For example, threshold serum or saliva anti-nicotine antibody levels associated with a desired endpoint (e.g., a 20% chance of abstaining from smoking for at least 4 weeks) may vary among subjects that smoke fewer than about 10, about 10-20, about 20-30, about 30-40, or about 40 or more cigarettes per day, with threshold serum or saliva anti-nicotine antibody levels generally being lower for subjects that smoke fewer cigarettes per day. For example, a threshold serum level selected from at least about 6 µg/ml, at least about 10 µg/ml, at least about 12 µg/ml, at least about 15 µg/ml, at least about 20 µg/ml, or at least about 25 µg/ml (including at least 6 µg/ml, at least 10 µg/ml, at least 12 µg/ml, at least 15 µg/ml, at least 20 µg/ml, and at least 25 µg/ml) may be correlated with subjects that smoke fewer than about 30 cigarettes per day, such as fewer than about 10, about 10-20, or about 20-30 cigarettes per day (including fewer than 10, 10-20 and 20-30 cigarettes per day), while a threshold serum level of up to least about 25 µg/ml (including the lower levels exemplified above), at least about 30 µg/ml, at least about 35 µg/ml, at least about 40 µg/ml, at least about 45 µg/ml, at least about 50 µg/ml, or more, may be correlated with subjects that smoke 30 or more cigarettes per day, such as about 30-40 or about 40 or more cigarettes per day (including 30-40 or 40 or more). The practitioner can determine corresponding secreted antibody levels using routine methodologies.

In accordance with some embodiments, the threshold serum or saliva anti-nicotine antibody level is directly correlated with the number of cigarettes smoked per day, such as the number of cigarettes smoked on the day before a target quit date (or within 1-3 days of a target quit date) or as a recent average of the number of cigarettes smoked per day (for example averaged over the week prior to the target quit date). For example, the threshold serum anti-nicotine antibody level (in µg/ml) may be from about 1.5 to about 2.0 times the number of cigarettes smoked per day, such as the number of cigarettes smoked on the day before a target quit date, including about 1.5, 1.6, 1.7, 1.8, 1.9 and 2.0 times the number of cigarettes smoked per day. For example, a subject who smoked 10 cigarettes on the day before a target quit date may have a threshold serum anti-nicotine antibody level of from about 15 to about 20 µg/ml, including about 18 µg/ml; while a subject who smoked 20 cigarettes on the day before a target quit date may have a threshold serum anti-nicotine antibody level of from about 30 to about 40 µg/ml, including about 36 µg/ml. The practitioner can determine corresponding secreted antibody levels using routine methodologies.

In accordance with some embodiments, the invention relates to determining whether a subject should be administered a nicotine immunogenic composition (e.g., a composition that induces anti-nicotine antibodies in the subject or elevates the levels of ant-nicotine antibodies in the subject), e.g., determining whether it is an advantageous time to administer a nicotine immunogenic composition, such as determining whether it is an advantageous time for a subject who has been administered a dose of a nicotine immunogenic composition to be administered a subsequent dose of a nicotine immunogenic composition. For example, if the subject's serum anti-nicotine antibody levels are not at or above a threshold level, a determination may be made that the subject should be administered a nicotine immunogenic composition, while if the subject's serum anti-nicotine antibody levels are at least a threshold level, a determination may be made that the subject should not be administered a nicotine immunogenic composition. Suitable threshold levels include those described above, e.g., about 6 µg/ml, about 10 µg/ml, about 12 µg/ml, about 15 µg/ml, about 20 µg/ml, about 25 µg/ml, about 30 µg/ml, about 35 µg/ml, about 40 µg/ml, about 45 µg/ml, about 50 µg/ml, or more, or from about 1.5 to about 2.0 times the subject's number of cigarettes smoked per day for serum antibody levels. The practitioner can determine corresponding secreted antibody levels using routine methodologies.

The threshold level for determining whether it is an advantageous time to quit smoking may be the same as or different from the threshold level for determining whether it is an advantageous time to administer a nicotine immunogenic composition. For convenience, the threshold level for determining whether it is an advantageous time to quit smoking is referred to herein as the "first specified threshold level," while the threshold level for determining whether it is an advantageous time to administer a nicotine immunogenic composition is referred to herein as the "second specified threshold level."

In some embodiments, the nicotine immunogenic composition is a nicotine vaccine that comprises a nicotine-carrier conjugate, as described above. For example, any of the nicotine-carrier conjugates described in, for example, U.S. Pat. No. 6,232,082 (Ennifar), U.S. App. 2007/0129551 A1 (Ennifar), U.S. Pat. No. 5,876,727 (Swain) and U.S. Pat. No. 6,932,971 (Bachmann) can be used, including nicotine-carrier conjugates comprising 3'aminomethylnicotine, such as 3'aminomethylnicotine conjugated to recombinant exoprotein A, including the NicVAX® product made by Nabi Biopharmaceuticals (Rockville, Md.).

In some embodiments, the subject has previously been administered a nicotine immunogenic composition, and the methods described herein comprise administering (or counseling to have administered) a subsequent or "booster" dose of the nicotine immunogenic composition. In other embodiments, the subject has previously been administered a first nicotine immunogenic composition, and the methods described herein comprise administering (or counseling to have administered) a second nicotine immunogenic composition that is different from the first nicotine immunogenic composition, such as by comprising a different antigenic component (e.g., a different nicotine-carrier conjugate) or different formulation. Regardless of whether the same or different immunogenic composition is used, the dosage of the nicotine immunogenic composition administered (or counseled to be administered) in accordance with the methods described herein may be the same as, greater than, or lower than, the dosage of any nicotine immunogenic composition previously administered to the subject.

In some embodiments, the methods described herein are preceded by administering to the subject a nicotine immunogenic composition, as described above.

Devices

In accordance with some embodiments, the invention provides devices for determining a specified threshold serum or saliva anti-nicotine antibody level. In some embodiments, the device comprises (a) a user interface configured to receive at least one user input, such as an input indicative of at least one factor selected from the group consisting of the subject's degree of nicotine addiction (such as one or more of the factors described above), the level of counseling the subject receives, and the number of doses of a nicotine immunogenic composition the subject has received; (b) a processing circuit configured to calculate a specified threshold serum or saliva anti-nicotine antibody level based on the at least one user input; and (c) an output device configured to provide an output signal indicative of the specified threshold serum or saliva anti-nicotine antibody level. The device may be configured to determine a first and/or a second specified threshold serum or saliva anti-nicotine antibody level, as described above.

Figure 10:
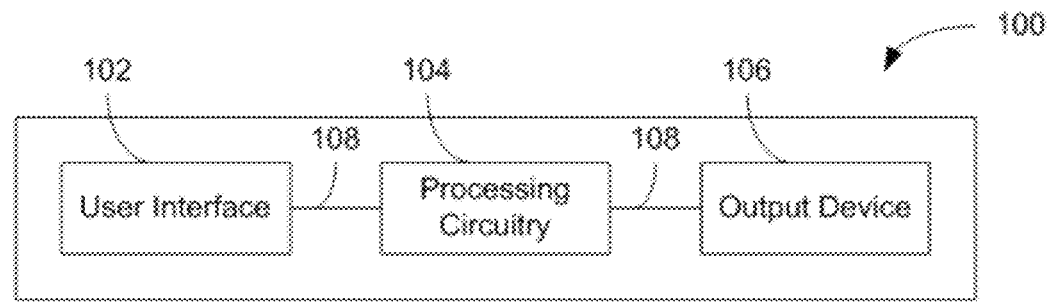
FIG. 10 depicts a device for determining a specified threshold serum or saliva anti-nicotine antibody level according to an exemplary embodiment.

One embodiment of a device 100 for determining a specified threshold serum or saliva anti-nicotine antibody level is depicted in FIG. 10. Device 100 includes a user interface 102, processing circuitry 104, and an output device 106. User interface 102, processing circuitry 104, and output device 106 are communicably coupled by communication links 108. In some embodiments, user interface 102 may be any suitable, mechanical, electronic or computer interface. For example user interface 102 may include any suitable input device such as a keyboard, mouse, bar code reader, dial, etc. In other embodiments, user interface 102 may be a form supplied by a server to a user via a network (e.g., the internet, LAN, etc.). User interface 102 may receive one or more input indicative of the subject's degree of nicotine addiction (such as one or more of the factors described above), the level of counseling the subject receives, and/or the number of doses of a nicotine immunogenic composition the subject has received. Processing circuitry 104 calculates a specified threshold serum or saliva anti-nicotine antibody level based on the user input received by user interface 102. Output device 106 may be any device suitable to provide an output signal indicative of the specified threshold serum or saliva anti-nicotine antibody level. In one embodiment, output device 106 may be a display device (e.g., monitor, screen, etc.) to display the specified threshold serum or saliva anti-nicotine antibody level calculated by processing circuitry 104. In other embodiments output device 106 may be a printer, speaker, disk drive, CD/DVD writer, etc. In yet another embodiment, output device 106 may be an electronic output device to transmit the output signal for storage in a database or other computer memory structure. In another embodiment, output device 106 may be configured to communicate directly with one of the devices as shown and described in relation to FIGS. 11 and 12 to provide the specified threshold serum or saliva anti-nicotine antibody level for processing as discussed below.

In another embodiment, a computer program product including a computer usable medium having computer readable program code embodied therein is provided. The computer readable program code is adapted to be executed to implement one or more of the embodiments or methods disclosed herein. In one such embodiment, the computer readable program code may be executed to receive one or more input indicative of the subject's degree of nicotine addiction (such as one or more of the factors described above), the level of counseling the subject receives, and/or the number of doses of a nicotine immunogenic composition the subject has received. The program code may then be executed to calculate a specified threshold serum or saliva anti-nicotine antibody level based on the input and to generate an output signal indicative of the specified threshold serum or saliva anti-nicotine antibody level. The output signal may be displayed, printed, stored in memory, etc.

In accordance with some embodiments, the invention provides devices for determining whether it is an advantageous time for a subject to quit smoking, In some embodiments, the device comprises (a) a sensor configured to contact a biological sample from the subject (such as a serum, blood or saliva sample) containing a level of anti-nicotine antibodies, the sensor configured to provide a sensor output signal based upon the level of anti-nicotine antibodies in the biological sample; (b) a processing circuit communicably coupled to the sensor, the processing circuit configured to determine the level of anti-nicotine antibodies present in the biological sample based on the sensor output signal; and (c) an output device configured to generate an output based upon the determined level of anti-nicotine antibodies present in the biological sample.

In some embodiments, the processing circuit is further configured to compare the determined level of anti-nicotine antibodies present in the biological sample to a first specified threshold serum or saliva anti-nicotine antibody level, and the output device is further configured to generate at least one of (i) a first output, if the determined level of anti-nicotine antibodies is at or above the first specified threshold serum or saliva anti-nicotine antibody level, to indicate that it is an advantageous time for the subject to quit smoking and (ii) a second output, if the determined level of anti-nicotine antibodies is below the first specified threshold serum or saliva anti-nicotine antibody level, to indicate that it is not an advantageous time for the subject to quit smoking.

Figure 11:
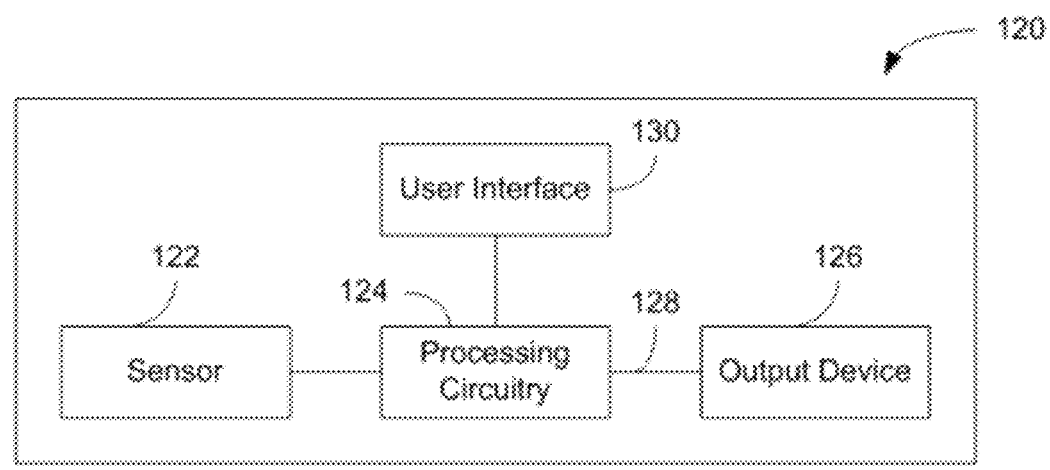
FIG. 11 illustrates a device for determining whether it is an advantageous time for a subject to quit smoking according to an exemplary embodiment.

Referring to FIG. 11, a device 120 is shown. Device 120 includes a sensor 122, processing circuitry 124, and an output device 126. In some embodiments device 120 includes a user interface 130 (e.g., any suitable, mechanical, electronic or computer interface). Communicably coupling the elements of device 120 are communication links 128.

Device 120, as with any other device described herein, optionally includes a suitable power supply (e.g., battery, AC power supply, photovoltaic cell, etc.) to provide power to one or more components of the device.

Sensor 122 may be any sensor configured to contact a biological sample from the subject (such as a serum, blood, saliva samples, etc.) containing a level of anti-nicotine antibodies and configured to provide an output signal based upon the level of anti-nicotine antibodies in the biological sample. Sensor 122 may be an electronic sensor, chemical sensor, etc. Sensor 122 may generate an electronic output signal, a chemical output signal, a light-based output signal, etc. If the output signal is not in a form readily useable by processing circuitry 124, device 120 may include appropriate components to convert the output signal to a useable form. For example, device 120 may include a light sensitive element (e.g., charge-coupled device (CCD), etc.) to convert a light-based output signal to an electronic signal.

The output signal is received by processing circuitry 124. In one embodiment, processing circuitry 124 is configured to determine the level of anti-nicotine antibodies present in the biological sample based on the sensor output signal. Output device 126 is configured to generate an output based upon the determined level of anti-nicotine antibodies present in the biological sample. As discussed below, output device 126 may generate an observable signal, such as a visual, electronic, optical, aural (audible), or magnetic signal, to indicate the determined level of anti-nicotine antibodies present in the biological sample.

In another embodiment, processing circuitry 124 is configured to compare the determined level of anti-nicotine antibodies present in the biological sample to a first specified threshold serum or saliva anti-nicotine antibody level. In this embodiment, output device 126 is configured to generate at least one of (i) a first output if the determined level of anti-nicotine antibodies is at or above the first specified threshold serum or saliva anti-nicotine antibody level, to indicate that it is an advantageous time for the subject to quit smoking, and (ii) a second output if the determined level of anti-nicotine antibodies is below the first specified threshold serum or saliva anti-nicotine antibody level, to indicate that it is not an advantageous time for the subject to quit smoking. In one such embodiment, processing circuitry 124 is configured to provide a control signal to output device 126 to instruct output device 126 to generate either the first or second output.

In various embodiments, the first specified threshold serum or saliva anti-nicotine antibody level may be provided to device 120 in a variety of ways. In one embodiment, the first specified threshold serum or saliva anti-nicotine antibody level may be calculated based on at least one user input received by user interface 130. In this embodiment, processing circuitry 124 may be configured to determine the threshold level as discussed above regarding device 100. In another embodiment, the first specified threshold serum or saliva anti-nicotine antibody level may be retrieved from a database or received from another device, such as device 100 of FIG. 10.

In some embodiments, the elements of device 120 may be integrated into a single housing or body made of suitable material (e.g., plastic, metal, etc.). In one embodiment, device 120 is formed similar to a oral digital thermometer in which sensor 122 is located a one end for insertion into a subject's mouth, with processing circuitry 124 located within the body of device 120. In this embodiment, output device 126 may include an LED screen for displaying the output and/or a speaker for generating an audible output. In another embodiment, device 120 may include a needle (similar to a needle or pin of a digital blood glucose meter) for puncturing a subject's skin to bring a small amount of blood into contact with sensor 122, or the device can include a dipstick for contacting as described in more detail below.

Further, in other embodiments, device 120 may include distributed or physically separate components. For example, sensor 122 may be a chemical embedded on a test strip of suitable material (e.g., paper, fabric, cardboard, etc.), and processing circuitry 124 and output device 126 may be a separate device (e.g., scanner, reader, etc.) configured to detect the signal generated by sensor 122. In another embodiment, processing circuitry 124 and output device 126 may be located in a central location (e.g., lab, doctor's office, etc.) that receives (e.g., via mail, hand delivery, etc.) the test strip or other housing including sensor 122 for analysis. In such an embodiment, the level of anti-nicotine antibodies present in the biological sample may be determined and compared to the first specified threshold serum or saliva anti-nicotine antibody level at the central location, and then the results may be communicated to the subject via suitable means (e.g., telephone, mail, email, etc.).

In another embodiment, processing circuitry 124 may be configured to perform various diagnostic testing to determine whether or not device 120 is working properly and/or whether or not a particular detection test has run correctly. In such an embodiment, output device 126 may be configured to generate an output indicative of whether or not device 120 is working properly and/or whether or not a particular detection test has run correctly. For example, output device 126 may be a LED display that displays a particular color (e.g., red) or icon (e.g., "error") if an error is detected. In another embodiment, output device 126 may provide an indication of the type of error that occurred. For example, output device 126 may display a message that the sample volume was too low, that processing was interrupted, etc. In another embodiment, output device 126 may also be configured to generate an output indicative of appropriate action for the user to take to correct the error. For example, output device 126 may generate a message instructing the user to replace the sensor, to replace the battery, to download a software update, use a larger sample volume, etc. In addition, processing circuitry 124 may be configured to perform calibration procedures to calibrate device 120.

Figure 12:
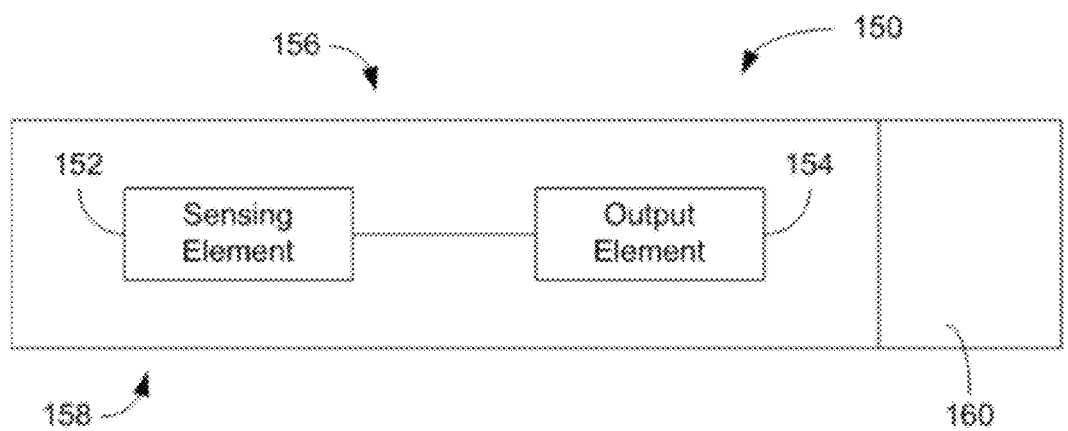
FIG. 12 illustrates a device for determining whether it is an advantageous time for a subject to quit smoking according to another exemplary embodiment.

In other embodiments, as shown in FIG. 12, the device comprises (a) a sensing element configured to contact a biological sample from the subject, the sensing element configured to generate an output signal indicative of the level of anti-WASH nicotine antibodies in the biological sample; and (b) an output element responsive to the output signal generated by the sensing element, the output element configured to generate at least one of (i) a first output, if the determined level of anti-nicotine antibodies is at or above a first specified threshold serum anti-nicotine antibody level, to indicate that it is an advantageous time for a subject to quit smoking and (ii) a second output, if the determined level of anti-nicotine antibodies is below a first specified threshold serum anti-nicotine antibody level, to indicate that it is not an advantageous time for a subject to quit smoking.

Referring to FIG. 12, a device 150 is shown according to another exemplary embodiment. Device 150 includes a sensing element 152 in communication with an output element 154. Sensing element 152 is configured to contact a biological sample from the subject, and output element 154 is configured to generate an output signal indicative of the level of anti-nicotine antibodies in the biological sample. For example, output element 154 may be responsive to the output signal generated by sensing element 152 to generate a first output, if the determined level of anti-nicotine antibodies is at or above a first specified threshold serum anti-nicotine antibody level, to indicate that it is an advantageous time for a subject to quit smoking. Additionally or alternatively, output element 154 may be responsive to the output signal generated by sensing element 152 to generate a second output if the determined level of anti-nicotine antibodies is below a first specified threshold serum anti-nicotine antibody level, to indicate that it is not an advantageous time for a subject to quit smoking. In one such embodiment, sensing element 152 is a chemical agent reactive to the level of anti-nicotine antibodies in the biological sample. The output signal generated by sensing element 152 may be any change capable of causing output element 154 to generate the first and/or second output as discussed above. For example, the output signal generated by sensing element 152 may be a change in shape, pH, conductivity, etc. that triggers the output to be generated by output element 154.

In one embodiment, sensing element 152 is a chemical embedded on or in a test strip made of suitable material (e.g., paper, cardboard, fabric, plastic, etc.) or a dipstick made of suitable material (e.g., cardboard, plastic, etc.). In such an embodiment, output element 154 may be a chemical that changes color in response to the reaction of sensing element 152. Device 150 may comprise a body 156 or stick of suitable material (e.g., plastic, cardboard, etc.) for supporting sensing element 152 and output element 154. In this embodiment, the body of device 150 may include a handle portion 160 to allow the user to conveniently hold device 150 during the application of the biological sample or during reading of the output (e.g., handle portion 160 may be located at an end of body 156 generally opposite of end 158 that includes sensing element 152). In one such embodiment, device 150 may be a dipstick having handle portion 160 to allow a user to grip device 150 while inserting sensing element 152 into a container containing a biological sample. In another embodiment, device 150 is shaped like an oral thermometer for directly placing sensing element 152 in a subject's mouth. In yet another embodiment, device 150 may include a calorimetric assay.

In any of the foregoing embodiments, the device may include a user interface (e.g., a mechanical, electronic or computer interface), such as user interface 102 or 130, configured to receive at least one user input, such as a mechanical, electronic or computer interface, such as an input indicative of at least one factor selected from the group consisting of the subject's degree of nicotine addiction (such as one or more of the factors described above), the level of counseling the subject receives, and the number of doses of a nicotine immunogenic composition the subject has received. In accordance with such embodiments, the specified threshold serum or saliva anti-nicotine antibody level may be based on the at least one user input, e.g., correlated with at least one of the factors. In another embodiment, the first specified threshold serum or saliva anti-nicotine antibody level may be retrieved from a database or received from another device, such as the device of FIG. 10.

In accordance with some embodiments, the invention provides devices for determining whether it is an advantageous time for a subject who has been administered a dose of a nicotine immunogenic composition to be administered a subsequent dose of a nicotine immunogenic composition. In some embodiments, the device comprises (a) a sensor, such as sensor 122, configured to contact a biological sample from the subject containing a level of anti-nicotine antibodies, the sensor configured to provide a sensor output signal based upon the level of anti-nicotine antibodies in the biological sample; (b) a processing circuit, such as processing circuitry 124, communicably coupled to the sensor, the processing circuit configured to determine the level of anti-nicotine antibodies present in the biological sample based on the sensor output signal and to compare the determined level of anti-nicotine antibodies present in the biological sample to a second specified threshold serum anti-nicotine antibody level; and (c) an output device, such as output device 126, configured to generate at least one of (i) a first output, if the determined level of anti-nicotine antibodies is not at or above the second specified threshold serum anti-nicotine antibody level, to indicate that it is an advantageous for the subject to be administered a subsequent dose of a nicotine immunogenic composition and (ii) a second output, if the determined level of anti-nicotine antibodies is above the second specified threshold serum anti-nicotine antibody level, to indicate that it is not an advantageous time for the subject to be administered a subsequent dose of a nicotine immunogenic composition.

In other embodiments, the device comprises (a) a sensing element, such as sensing element 152, configured to contact a biological sample from the subject, the sensing element configured to generate an output signal indicative of the level of anti-nicotine antibodies in the biological sample; and (b) an output element, such as output element 154, responsive to the output signal generated by the sensing element, the output element configured to generate at least one of (i) a first output, if the determined level of anti-nicotine antibodies is not at or above a second specified threshold serum anti-nicotine antibody level, to indicate that it is an advantageous time for the subject to be administered a subsequent dose of a nicotine immunogenic composition and (ii) a second output, if the determined level of anti-nicotine antibodies is above the second specified threshold serum anti-nicotine antibody level, to indicate that it is not an advantageous time for the subject to be administered a subsequent dose of a nicotine immunogenic composition.

In some embodiments, a single device is provided that combines the functionality of one or more of the devices discussed herein. For example, in one embodiment, device 120 is configured to compare the determined level of anti-nicotine antibodies present in the biological sample to a first specified threshold serum or saliva anti-nicotine antibody level to determine if it is an advantageous time for the subject to quit smoking and to compare the determined level of anti-nicotine antibodies present in the biological sample to a second specified threshold serum anti-nicotine antibody level to determine if it is an advantageous time for the subject to be administered a subsequent dose of a nicotine immunogenic composition. In this embodiment, output device 126 may be configured to two to four outputs, such as one or two outputs, to indicate whether or not it is an advantageous time for the subject to quit smoking and/or one or two outputs to indicate whether or not it is an advantageous time for the subject to be administered a subsequent dose of a nicotine immunogenic composition. Similarly, in another exemplary embodiment, device 150 is configured to generate two to four outputs, such as one or two outputs to indicate whether or not it is an advantageous time for the subject to quit smoking and/or one or two outputs to indicate whether or not it is an advantageous time for the subject to be administered a subsequent dose of a nicotine immunogenic composition.

In some embodiments, there are provided devices that comprise the features of two or more of the devices outlined above, such as a device for (i) determining a specified threshold serum or saliva anti-nicotine antibody level and/or (ii) for determining whether it is an advantageous time for a subject to quit smoking, and/or (iii) for determining whether it is an advantageous time for a subject who has been administered a dose of a nicotine immunogenic composition to be administered a subsequent dose of a nicotine immunogenic composition.

The devices described herein may be designed for use by a clinician or by a lay person, such as the subject. In one particular embodiment, the device is used by contacting a portion of the device with a blood or saliva sample from the subject and observing an analytical result, such as where the device is a dipstick type device, or comprises a dipstick type element for contacting with the subject's serum or saliva. In specific embodiments, the user need only perform the contacting step before an analytical result can be observed, such as the result of a colorometric assay or other signal generated by the device.

In some embodiments, the device produces an observable signal (output), such as a visual, electronic, optical, aural (audible), or magnetic signal, that is correlated with the measured level of anti-nicotine antibodies in the sample, as outlined above. In some embodiments, the signal (output) is generated by a chemical or biochemical reaction, such as may occur in a colorimetric assay. In some embodiments, the signal indicates the measured level of anti-nicotine antibodies in the sample, such as through a numerical display (e.g., in µg/ml). In other embodiments, the signal indicates that the measured level of anti-nicotine antibodies is within a specified range or is at least a specified threshold level, such as at least a first or second specified threshold level (e.g., at least about 6 µg/ml, at least about 12 µg/ml, at least about 15 µg/ml, at least about 20 µg/ml, or at least about 25 µg/ml, greater than about 25 µg/ml), such as by displaying a numerical character or visual symbol correlated with a specified range or specified threshold level. For example, a given number, letter, color, intensity, shape (e.g., "+" or "−"), or other visual symbol, or an audible sound or other observable signal, may be correlated with a specified range or specified threshold level. Analytical test devices useful for detecting and quantifying antibodies present in a sample are known in the art.

In some embodiments, the device produces a signal indicating that the measured level is at least the threshold antibody level and/or a signal indicating that the measured level is less than the threshold antibody level, as outlined above.

In some embodiments, the device includes a mechanical or electronic or computer device or interface by which the user can input an input indicative of at least one factor selected from the group consisting of the subject's degree of nicotine addition (such as one or more of the factors described above), the level of counseling the subject receives, and the number of doses of a nicotine immunogenic composition the subject has received. For example, the device may include a mechanical or electronic or computer device or interface by which the user can input an input indicative of the subject's number of cigarettes smoked per day, such as a mechanical dial or keypad or an electronic input device (e.g., electronic keypad). In some embodiments, such a device also includes a mechanical or electronic display of a threshold antibody level correlated with the subject's number of cigarettes smoked per day, such as a mechanical dial or electronic output device (e.g., electronic display screen) that displays a threshold antibody level correlated with the subject's number of cigarettes smoked per day. In other embodiments, the device produces an observable signal, such as a visual, optical, aural, magnetic or electronic signal as described above, indicating whether the measured level of antibodies is at least a threshold antibody level correlated with the subject's number of cigarettes smoked per day.

The processing circuitry discussed herein may be a general purpose processor, an application specific processor (ASIC), a circuit containing one or more processing components, a group of distributed processing components, a group of distributed computers configured for processing, etc., configured provide the functionality discussed herein. The processing circuitry may include or be communicably coupled to memory as needed. Memory (e.g., memory unit, memory device, storage device, etc.) may be one or more devices for storing data (e.g., data related to the determined threshold, the measured antibody level, etc.) and/or computer code for completing and/or facilitating the various processes described in the present disclosure. Memory may include volatile memory and/or non-volatile memory. Memory may include database components, object code components, script components, and/or any other type of information structure for supporting the various activities described in the present disclosure. Any distributed and/or local memory device of the past, present, or future may be utilized with the systems and methods of this disclosure. A single memory unit may include a variety of individual memory devices, chips, disks, and/or other storage structures or systems. Any of the devices discussed herein may include a removable memory component to facilitate transfer of data between devices.

Processing circuitry discussed herein may include computer code (e.g., object code, program code, compiled code, script code, executable code, or any combination thereof) for performing the functions, calculations, etc. discussed herein.

Any of the components of the devices discussed herein may include one or more communication interface component for communicably coupling the components via the communication links. The communication links may include a circuit or any other wired link, wireless link, or network connection. The communication interface may include one or more jacks or other hardware for physically coupling communication links to each component, an analog to digital converter, a digital to analog converter, signal processing circuitry, and/or other suitable components. Communication interface may include hardware configured to connect the components of via wireless connections. The devices discussed herein may also include any other software or hardware needed to support communication between the various components (e.g., negotiating connections, communication via standard or proprietary protocols, etc.).

Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Figure 13:
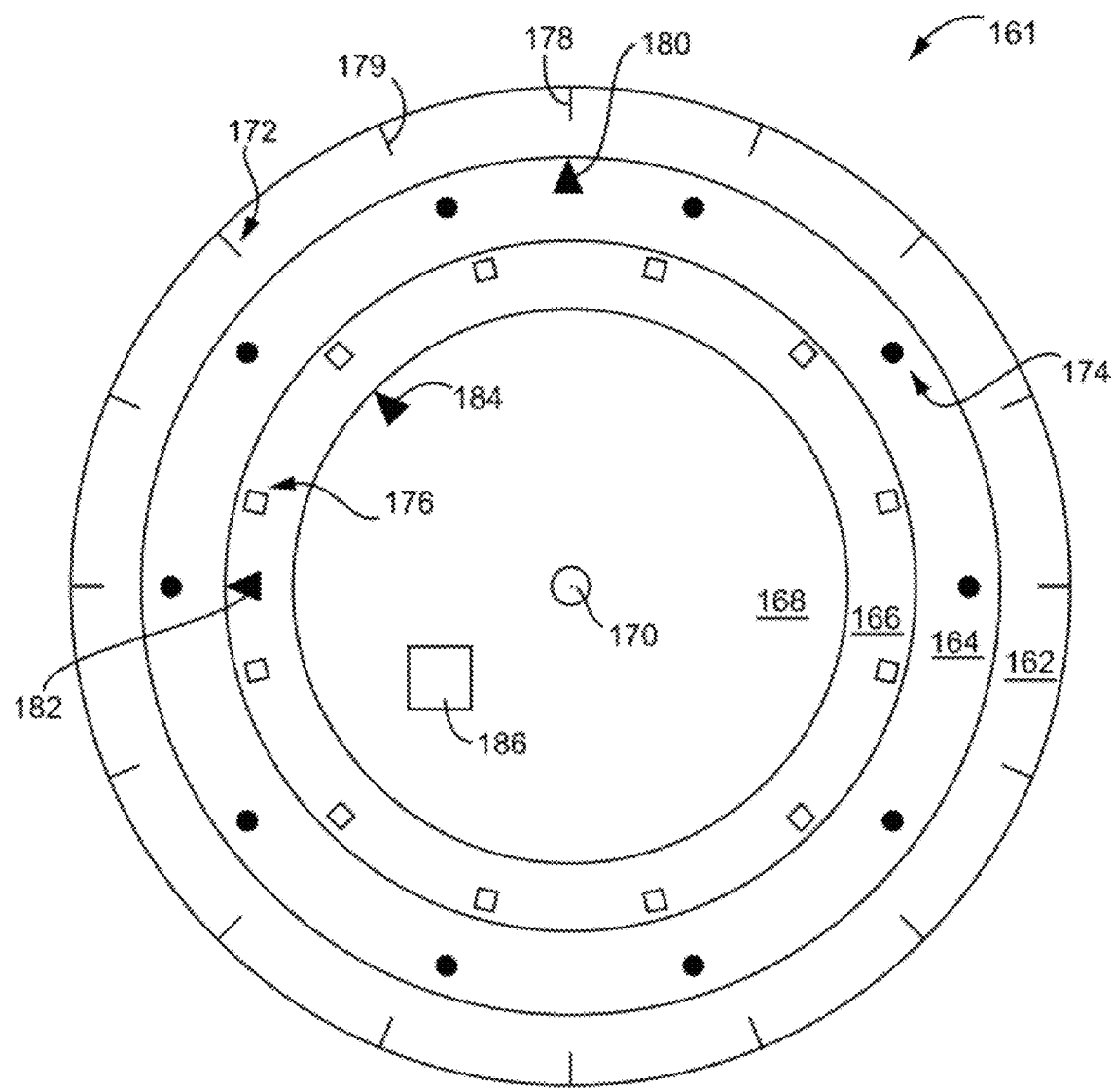
FIG. 13 illustrates a device for determining whether it is an advantageous time for a subject to quit smoking according to an exemplary embodiment.

Referring to FIG. 13, a device 161 for determining a threshold or minimum antibody level for a subject is shown. Device 161 includes first wheel 162, second wheel 164, third wheel 166, and fourth wheel 168. Wheels 162, 164, 166 and 168 are rotatably mounted together via hub 170 such that each of wheels 162, 164, 166 and 168 are permitted to be individually rotated about hub 170. In the embodiment shown, wheel 162 is the bottom wheel. Wheel 164 is mounted on top of wheel 162. Wheel 166 is mounted on top of wheel 164. Wheel 168 is mounted on top of wheel 166.

Wheels 162, 164 and 166 include indicia 172, 174 and 176, respectively. Indicia 172, 174 and 176 each represent one of the factors upon which the determination of a threshold or minimum antibody level for a subject is made, as discussed in detail herein. For instance, indicia 172 may represent the degree of addiction, as measured by the baseline smoking level, by the number of cigarettes smoked immediately prior to the measure of anti-nicotine antibodies, or by a questionnaire; the number of previous quite attempts made within a certain period of time; the total number of years smoked; the total number of continuous years smoked; or how soon in the morning after awakening on a given day the subject craves of actually lights the first cigarettes or consumes other form(s) of nicotine Other factors represented on the wheels may be one or more of the level of counseling the subject receives and/or the number of doses of a nicotine immunogenic composition the subject has received.

In one embodiment, each wheel has a title or other label indicating the factor associated with the wheel. Further, each indicia 172, 174 and 176 include multiple individual marks that are representative of a particular value of the factor associated with the indicia of the wheel. For example, if indicia 172 represent the factor of the number of years that a person has smoked, the top most mark 178 may be associated with 10 years of smoking, and mark 179 immediately to the left of mark 178 may be associated with 9 years of smoking.

As can be seen in FIG. 13, the diameter of each wheel is smaller than the wheel below it, such that the portion of each wheel displaying indicia 172, 174 and 176 is not covered by the adjacent wheel. In addition, wheels 164, 166 and 168 include alignment marks 180, 182 and 184, respectively. Wheel 168 also includes an answer window 186.

To determine a threshold or minimum antibody level for a subject to quit smoking, the user of device 161 will rotate wheel 164 relative to wheel 162 to align alignment mark 180 with the appropriate mark within indicia 172 for the subject (e.g., alignment mark 180 is aligned with mark 178 if the subject has been smoking for 10 years). The user then rotates wheel 166 relative to wheel 164 to align alignment mark 182 with the appropriate mark within indicia 174 and then rotates wheel 168 relative to wheel 166 to align alignment mark 184 with the appropriate mark within indicia 176. With each of the wheels aligned with the appropriate mark within indicia 172, 174 and 176, answer window 186 will align with information printed on one of the wheels below wheel 168 to provide an indication of at least one of a first threshold antibody level, a second threshold antibody level and a minimum antibody level, such as a numerical representation of the antibody level.

In some embodiments, one of the wheels represents the subject's measured antibody level, and the device can be used to determine whether or not it is an advantageous time for the subject to quit smoking, whether or not it is an advantageous time for the subject to have administered a dose of a nicotine immunogenic composition. For example, the device is used as discussed above, and the answer window will align with information printed on one of the wheels below to provide an indication of whether or not it is an advantageous time for the subject to quit smoking, and/or whether or not it is an advantageous time for the subject to have administered a dose of a nicotine immunogenic composition, such as by a yes/no indication, a quit/don't quit indication, a quit/wait indication, a dose/don't dose indication, etc., a red/green indication, or any other indicator to indicate the determination(s).

The wheels of device 161 may be made of any suitable material (e.g., paper, cardboard, plastic, etc.). While FIG. 13 shows device 161 including four wheels, device 161 may include any other number of wheels depending on the number of factors to be used in making the determination. Further, while device 161 is described for determining a threshold or minimum antibody level, it should be understood that device 161 may be designed to make any other determination discussed in any of the other exemplary embodiments disclosed herein. For example, as noted above, in another embodiment, device 161 may be configured for determining whether it is an advantageous time for a subject who has been administered a dose of a nicotine immunogenic composition to be administered a subsequent dose of a nicotine immunogenic composition. In yet another embodiment, device 161 may be configured for prolonging smoking abstinence (increasing the duration of abstinence) in a subject who has quit smoking.

Device 161 may be configured for use at home by a lay person, such as the subject. In such an embodiment, device 161 may include fewer wheels to simplify use or may only include wheels related to factors that the subject is able to address without the aid of a professional, such as a doctor. In another embodiment, device 161 may be configured for use by a clinician or other professional. In such an embodiment, device 161 may include more wheels or may include wheels related to factors that the professional is able to answer (e.g., the measured level of anti-nicotine antibodies present in the biological sample).

Kits

The present invention includes kits for determining an advantageous time, and whether it is an advantageous time, for a subject to quit smoking. In some embodiments, the kits comprise (a) an agent that specifically binds anti-nicotine antibodies; (b) instructions to use the agent to measure the level of anti-nicotine antibodies in serum or saliva from a subject; and (c) instructions indicating that serum or saliva anti-nicotine antibody levels of at least a threshold level indicate an advantageous time to quit smoking, and/or that serum or saliva anti-nicotine antibody levels below the first specified threshold level do not indicate that it is an advantageous time for the subject to quit smoking.

In some embodiments, the threshold serum antibody level is at least about 6 µg/ml anti-nicotine antibodies. In other embodiments, the threshold level is at least about 10 µg/ml, at least about 12 µg/ml, at least about 15 µg/ml, at least about 20 µg/ml, or at least about 25 µg/ml. Thus, for example, the instructions may indicate that serum anti-nicotine antibody levels of at least 6 µg/ml, at least 10 µg/ml, at least 12 µg/ml, at least 15 µg/ml, at least 20 µg/ml, or at least 25 µg/ml, indicate an advantageous time to quit smoking. The practitioner can determine corresponding secreted antibody levels using routine methodologies.

As discussed above, the threshold antibody level may be correlated with one or more of a variety of factors including but not limited to the subject's degree of addiction, the willingness of the subject to quit/abstain, and the amount of behavioral counseling the subject receives. Thus, for example, the instructions may correlate threshold serum or saliva anti-nicotine antibody levels with the subject's number of cigarettes smoked per day, such as by setting threshold serum anti-nicotine antibody levels (µg/ml) that are from about 1.5 to about 2.0 times the number of cigarettes smoked per day, including about 1.5, 1.6, 1.7, 1.8, 1.9 or 2.0 times the number of cigarettes smoked per day.

In some embodiments, the kit comprises an agent that specifically binds to anti-nicotine antibodies, as described above. In some embodiments, the kit comprises an anti-nicotine antibody standard solution which contains anti-nicotine antibodies, including standard solution which contains a known quantity of anti-nicotine antibodies.

In some embodiments, the kits described herein may include guidelines or instructions indicating that a nicotine immunogenic composition should be administered to the subject if the subject's serum anti-nicotine antibody levels are not at or above a threshold level, such as a second specified threshold level as described above. Suitable threshold levels include those described above, e.g., about 6 µg/ml, about 10 µg/ml, about 12 µg/ml, about 15 µg/ml, about 20 µg/ml, about 25 µg/ml, about 30 µg/ml, about 35 µg/ml, about 40 µg/ml, about 45 µg/ml, about 50 µg/ml, or more, or from about 1.5 to about 2.0 times the subject's number of cigarettes smoked per day. As discussed above, the threshold level for determining an advantageous time to quit smoking may be the same as or different from the threshold level for determining that a nicotine immunogenic composition should be administered.

In some embodiments, the kit includes a device as described above. Any of the above-described devices, and variations thereof that will be apparent to those skilled in the art, can be provided as kits suitable for clinical or home use. A kit may comprise a single device together with instructions for use, or it may comprise a plurality (e.g., two, three, four, five or more) of the devices. In one embodiment, each device is individually wrapped in moisture impervious wrapping. In one specific embodiment, each device is packaged together with appropriate instructions for use.

Methods

Also described herein are methods for determining an advantageous time for a subject to quit smoking, or for determining whether it is an advantageous time to quit smoking. For convenience, the discussion here refers to serum anti-nicotine antibody levels. As discussed above, the invention includes parallel methods practiced with reference to secreted anti-nicotine antibody levels, such as may be detected in saliva, In some embodiments, the method comprises (a) measuring the level of anti-nicotine antibodies in serum from the subject; and (b) correlating a threshold anti-nicotine antibody level with an advantageous time for the subject to quit smoking. In some embodiments, the threshold level is at least about 6 µg/ml anti-nicotine antibodies. In some embodiments, the method comprises (a) measuring the level of anti-nicotine antibodies in serum from the subject; and (b) determining that it is an advantageous time for a subject to quit smoking if the measured level is at or above a first specified threshold serum anti-nicotine antibody level, for instance one that indicates an advantageous time to quit smoking, or that it is not an advantageous time for a subject to quit smoking if the measured level is below the first specified threshold serum anti-nicotine antibody level. In some embodiments, the threshold level is at least about 6 µg/ml anti-nicotine antibodies.

In other embodiments, the threshold level is at least about 10 µg/ml, at least about 12 µg/ml, at least about 15 µg/ml, at least about 20 µg/ml, or at least about 25 µg/ml. Thus, for example, the method may comprise determining that it is an advantageous time to quit smoking when serum anti-nicotine antibody levels are at least 6 µg/ml, at least 10 µg/ml, at least 12 µg/ml, at least 15 µg/ml, at least 20 µg/ml, at least 25 µg/ml, at least about 30 µg/ml, at least about 35 µg/ml, at least about 40 µg/ml, at least about 45 µg/ml, and at least about 50 µg/ml, or determining that it is not an advantageous time to quit smoking when serum anti-nicotine antibody levels are below such a threshold level. In other embodiments, the threshold level is from about 1.5 to about 2.0 times the number of cigarettes smoked the day before the target quit date.

Also described are methods for counseling a subject on an advantageous time for the subject to quit smoking, or on whether it is an advantageous time for the subject to quit smoking. In some embodiments the method comprises (a) measuring the level of anti-nicotine antibodies in the serum of the subject; and (b) counseling the subject that it is an advantageous time for the subject to quit smoking, if the subject's serum anti-nicotine antibody levels is at or above a threshold level and/or that it is not an advantageous time for the subject to quit smoking, if the subject's serum anti-nicotine antibody levels is not at or above a threshold level, or is below a threshold level.

In some embodiments, the threshold level is at least about 6 µg/ml anti-nicotine antibodies. In other embodiments, the threshold level is at least about 10 µg/ml, at least about 12 µg/ml, at least about 15 µg/ml, at least about 20 µg/ml, at least about 25 µg/ml, at least about 30 µg/ml, at least about 35 µg/ml, at least about 40 µg/ml, at least about 45 µg/ml, and at least about 50 µg/ml. Thus, for example, the method may comprise counseling the subject that it is an advantageous time to quit smoking if the subject's serum anti-nicotine antibody levels are at least 6 µg/ml, at least 10 µg/ml, at least 12 µg/ml, at least 15 µg/ml, at least 20 µg/ml, at least 25 µg/ml, at least 30 µg/ml, at least 35 µg/ml, at least 40 µg/ml, at least 45 µg/ml, and at least 50 µg/ml, or counseling that it is not an advantageous time to quit smoking when serum anti-nicotine antibody levels are below such a threshold level.

As noted above, in some embodiments, the threshold antibody levels are correlated with one or more of a variety of factors including but not limited to the subject's degree of addiction, the subject's willingness to quit, and the amount of behavioral counseling the subject receives. For example, threshold antibody levels may be directly correlated with one or more of the above described factors associated with nicotine addiction, such that, for example, a higher threshold antibody level would pertain for a subject with a greater degree of addiction. Additionally, or alternatively, threshold antibody levels may be inversely correlated with the subject's willingness to quit and/or the amount of behavioral counseling the subject receives, such that, for example, a lower threshold antibody level would pertain for a subject receiving behavioral counseling. In accordance with these embodiments, the methods described above may further comprise, prior to step (b), determining at least one such factor. For example, the methods may include determining the subject's degree of addiction, such as, for example, may be indicated by one or more of the above described factors associated with nicotine addiction, and/or determining the amount of behavioral counseling the subject receives, and the threshold serum anti-nicotine antibody levels referenced in step (b) may be based on the subject's degree of addiction (direct correlation) and/or the amount of behavioral counseling the subject receives (inverse correlation).

As noted above, in some embodiments the threshold serum anti-nicotine antibody levels varies with the subject's number of cigarettes smoked per day. In accordance with these embodiments, the methods described above may further comprise, prior to step (b), determining the subject's number of cigarettes smoked per day, and the threshold serum anti-nicotine antibody levels referenced in step (b) may be based on the subject's number of cigarettes smoked per day, with threshold serum anti-nicotine antibody levels generally being lower for subjects that smoke fewer cigarettes per day. For example, a threshold level selected from at least about 6 µg/ml, at least about 10 µg/ml, at least about 12 µg/ml, at least about 15 µg/ml, at least about 20 µg/ml, or at least about 25 µg/ml (including at least 6 µg/ml, at least 10 µg/ml, at least 12 µg/ml, at least 15 µg/ml, at least 20 µg/ml, and at least 25 µg/ml) may be used for subjects that smoke fewer than about 30 cigarettes per day, such as fewer than about 10, about 10-20, or about 20-30 cigarettes per day (including fewer than 10, 10-20 and 20-30 cigarettes per day), while a threshold level of up to least about 25 µg/ml (including the lower levels exemplified above), at least about 30 µg/ml, at least about 35 µg/ml, at least about 40 µg/ml, at least about 45 µg/ml, at least about 50 µg/ml, or more, may be used for subjects that smoke more than 30 cigarettes per day, such as about 30-40 or about 40 or more cigarettes per day (including 30-40 or 40 or more). In other embodiments, the threshold level is from about 1.5 to about 2.0 times the number of cigarettes smoked per day, such as from about 1.5 to about 2.0 times the number of cigarettes smoked the day before a target quit date, as discussed in more detail above.

If the subject's serum anti-nicotine antibody levels are not at or above a threshold level (e.g., the "second" threshold antibody level), the above-described methods may further comprise administering to the subject a nicotine immunogenic composition (e.g., a composition that induces anti-nicotine antibodies in the subject or elevates the levels of ant-nicotine antibodies in the subject), and/or counseling the subject to have such a composition administered. Suitable threshold levels include those described above, e.g., about 6 µg/ml, about 10 µg/ml, about 12 µg/ml, about 15 µg/ml, about 20 µg/ml, about 25 µg/ml, about 30 µg/ml, about 35 µg/ml, about 40 µg/ml, about 45 µg/ml, about 50 µg/ml, or more, or from about 1.5 to about 2.0 times the subject's number of cigarettes smoked per day. As discussed above, the threshold level for determining an advantageous time to quit smoking may be the same as or different from the threshold level for determining that a nicotine immunogenic composition should be administered.

Suitable nicotine immunogenic compositions are described above.

As noted above, in other embodiments, the subject has previously been administered a first nicotine immunogenic composition, and the methods described herein comprise administering (or counseling to have administered) a second nicotine immunogenic composition that is the same as or different from the first nicotine immunogenic composition, such as by comprising a different antigenic component (e.g., a different nicotine-carrier conjugate) or different formulation. The dosage of the nicotine immunogenic composition administered (or counseled to be administered) in accordance with the methods described herein may be the same as, greater than, or lower than, the dosage of any nicotine immunogenic composition previously administered to the subject.

As noted above, in some embodiments, the methods described herein are preceded by administering to the subject a nicotine immunogenic composition, such as described above.

In general, the more doses of a nicotine immunogenic composition that a subject receives within a single course of treatment (e.g., within six months), the higher the individual's antibody levels will become. Accordingly, an advantageous time to quit smoking for a given subject, as assessed by threshold antibody level, can depend upon the number of doses that the subject already has received. Thus, in some embodiments of the kits, devices and methods described herein, the threshold antibody level is directly correlated with the number of doses of a nicotine immunogenic composition that the subject has received, such that, for example, a higher threshold antibody level would pertain for a subject who has received a greater number of doses, and a lower threshold antibody level would pertain for a subject who has received a lower number of doses. For example, threshold antibody levels may include at least about 25 µg/mL for subjects who have received up to two doses; at least about 50 µg/mL for subjects who have received three doses; at least about 75 µg/mL for subjects who have received four doses; and at least about 100 µg/mL for subjects who have received five doses. Thus, the number of doses of a nicotine immunogenic composition that a subject has received may be an additional or alternative factor used to determine the threshold antibody level for a subject in accordance with the methods, kits and devices described herein. Thus, the minimum levels described here may be adjusted upwards or downwards in consideration of one or more other factors discussed herein.

Any of the methods described herein can be used in conjunction with a machine or computer, or with any of the devices described above. For instance, a computer may be employed for transforming data related to any of the non-limiting factors described herein throughout (relating to, for example, nicotine addiction, willingness to quit, counseling, and number of doses received, the length of time since the subject has quit smoking) into a specified threshold or minimum serum anti-nicotine antibody level (as discussed in more detail below), and may include a mechanical or electronic device for receiving such data In some embodiments, the machine or computer can generate as output a first, second, and/or minimum threshold serum anti-nicotine antibody level. Thus, in some embodiments, the machine or computer includes a mechanical or electronic device for outputting a signal associated with first, second, and/or minimum threshold serum anti-nicotine antibody level, such as a numerical, calorimetric, symbolic, and/or audible output.

In some embodiments, the machine or computer is configured to receive as input the measured level of anti-nicotine antibodies in a subject. In some embodiments, the machine or computer includes a mechanical or electronic device for outputting the measured serum anti-nicotine antibody level, such as a numerical output of the measured serum anti-nicotine antibody level. In other embodiments, the machine or computer produces a signal indicating that the measured level is at least the first, second, or minimum threshold level as described herein, or is less than or greater than such level.

In other embodiments, the machine or computer is used in the kits, devices and methods for determining that it is or is not an advantageous time for a subject to quit smoking, and/or whether it is or is not an advantageous time for a subject who has been administered a dose of a nicotine immunogenic composition to be administered a subsequent dose of a nicotine immunogenic composition as discussed above and below.

All of these embodiments contemplate the optional use of written materials, such as printed materials or those that exist only electronically. Such printed materials may correlate any of the non-limiting factors described herein throughout (relating to, for example, nicotine addiction, willingness to quit, counseling, and number of doses received) with a specified threshold or minimum serum anti-nicotine antibody level.

Maintaining Abstinence

The invention also provides kits, devices and methods for increasing the duration of abstinence (maintaining abstinence) in a subject who has quit smoking (e.g. by preventing relapse). It has been discovered that by maintaining a minimum level of anti-nicotine antibodies (Cmin) above a certain level, a subject's duration of abstinence can be extended. Methods in accordance with this aspect of the invention include determining the level of anti-nicotine antibodies in the subject's serum (or saliva) and comparing the level to a minimum level. If the subject's anti-nicotine antibody levels are not at or above the minimum level, then the method comprises administering a nicotine immunogenic composition to the subject, or counseling the subject to have a nicotine immunogenic composition administered.

The minimum level for a given subject can depend upon one or more of a number of non-limiting factors discussed herein throughout. Exemplary minimum serum antibody levels include but are not limited to at least 5 µg/mL, at least 10 µg/mL, at least 15 µg/mL, at least 25 µg/mL, at least 35 µg/mL, and at least 45 µg/mL, and these can be upward or downward adjusted in accordance with such factors. In some embodiments, the subject's anti-nicotine antibody levels are measured at one or more times such as at least 1 month, at least 2 months, at least 3 months, at least 4 months, at least 6 months, at least 9 months, at least 12 months, at least 18 months, at least 24 months, or longer, after the subject has quit smoking. In some embodiments, the minimal level decreases over time, such that, for example, the minimum level for a subject being assessed 2 months after quitting smoking is greater than the minimum level for a subject being assessed 6 months after quitting smoking.

Devices in accordance with this aspect of invention also are provided, e.g., devices for prolonging smoking abstinence (increasing the duration of abstinence) in a subject who has quit smoking. In some embodiments, the device comprises (a) a sensor, such as sensor 122 discussed above, configured to contact a biological sample from the subject containing a level of anti-nicotine antibodies, the sensor configured to provide a sensor output signal based upon the level of anti-nicotine antibodies in the biological sample; (b) a processing circuit, such as processing circuitry 124 discussed above, communicably coupled to the sensor, the processing circuit configured to determine the level of anti-nicotine antibodies present in the biological sample based on the sensor output signal and to compare the determined level of anti-nicotine antibodies present in the biological sample to a minimum level; and (c) an output device configured to generate at least one of (i) a first output, if the determined level of anti-nicotine antibodies is not at or above the minimum level, to indicate that it is an advantageous time to administer a dose of a nicotine immunogenic composition to the subject in order to increase the duration of abstinence and (ii) a second output, if the determined level of anti-nicotine antibodies is above the minimum level, to indicate that it is not an advantageous time to time to administer a dose of a nicotine immunogenic composition to the subject in order to increase the duration of abstinence.

In other embodiments, the device comprises (a) a sensing element, such as sensing element 152 discussed above, configured to contact a biological sample from the subject, the sensing element configured to generate an output signal indicative of the level of anti-nicotine antibodies in the biological sample; and (b) an output element, such as output element 154 discussed above, responsive to the output signal generated by the sensing element, the output element configured to generate at least one of (i) a first output, if the determined level of anti-nicotine antibodies is not at or above a minimum level, to indicate that it is an advantageous time to administer a dose of a nicotine immunogenic composition to the subject in order to increase the duration of abstinence and (ii) a second output, if the determined level of anti-nicotine antibodies is above the minimum level, to indicate that it is not an advantageous time time to administer a dose of a nicotine immunogenic composition to the subject in order to increase the duration of abstinence.

In any of the foregoing embodiments, the device may include a user interface (e.g., user interface 102, or user interface 130 described above) configured to receive at least one user input, such as an input indicative of the duration of the subject's abstinence at the time of the assessment and optionally at least one factor selected from the group consisting of the subject's degree of nicotine addition (such as one or more of the factors described above), the level of counseling the subject receives, and the number of doses of a nicotine immunogenic composition the subject has received. In accordance with such embodiments, the minimum threshold serum or saliva anti-nicotine antibody level may be based on the at least one user input, e.g., correlated with the duration of the subject's abstinence, and optionally one or more other factors. In such embodiments, the processing circuitry of the device (e.g., processing circuitry 104, processing circuitry 124, described above) is configured to calculate the minimum threshold serum or saliva anti-nicotine antibody level based on the at least one user input. In this embodiment, the device may include an output device (e.g., output device 106, or output device 126 described above) to provide an output indicative of the calculated minimum threshold serum or saliva anti-nicotine antibody level.

These devices may include one or more features, components, or aspects as described above with reference to other devices including the devices of FIGS. 10, 11, and 12.

In some embodiments, the subject is enrolled in a NicVAX smoking cessation therapy program. For instance, NicVAX is more likely to succeed for smokers who have the desire to stop smoking and who are provided additional advice, support, and/or counseling during the quitting period. Therefore, NicVAX recipients may be offered the appropriate advice and counseling to support their quitting attempt.

In an exemplary embodiment, NicVAX (400 mg adsorbed to 1.1 µg aluminum) is administered to a subject via intramuscular injection, such as 1.0 mL per dose. Typical injection points include the deltoid region of the upper arm and the anterolateral area of the upper thigh. The subject receives a total of 6 injections of NicVAX that are administered at weeks 0, 4, 8, 12, 16, and 26. A successful quit is likely to occur when anti-nicotine antibody levels are at least a threshold level as described herein, and the subject may be instructed to set a target quit date at a time such as two weeks after the fourth administration of NicVAX. The subject is encouraged to continue to quit smoking even if the subject has lapses after the target quit date.

The embodiments described herein are not intended to be limiting. Thus, for example, any of the embodiments specifically described can be combined with one or more other embodiments also specifically described. All of these combinations and permutations are contemplated as part of the invention.

The following specific examples are included as illustrative only. These examples are in no way intended to limit the scope of the invention. Other aspects of the invention will be apparent to those skilled in the art to which the invention pertains.

EXAMPLE 1

Clinical Study

Nicotine-carrier conjugate—NicVAX® (Nabi Biopharmaceuticals, Rockville, Md.) is an investigational vaccine comprising a nicotine-carrier conjugate comprising 3'-aminomethylnicotine conjugated to recombinant exoprotein A. NicVAX® can be made by methods known in the prior art. See, for example, U.S. Pat. No. 6,232,082 (Ennifar) and U.S. App. 2007/0129551 A1 (Ennifar).

ELISA—An ELISA test was used to quantitate anti-nicotine antibodies in human serum or plasma samples. The method measures antigen-antibody specific interactions in microtiter plate wells coated with 3'-aminomethylnicotine conjugated to polyglutamic acid (3'AMNic-pGlu, antigen). The amount of antibody bound to antigen coated on the microtiter plate is determined by a subsequent reaction with anti-human Immunoglobulin ($IgG_\gamma$) antibody conjugated to horseradish peroxidase (HRP), followed by a chromogenic reaction with peroxidase substrate. The color development is measured at 450 nm.

Microtiter plates are coated with 3'AMNic-pGlu using 50 or 100 ng/mL 3'AMNic-pGlu in coating buffer (0.1M Phosphate buffer) and stored for at least 10 hours at 2-8° C. Plates are blocked with blocking solution (1% Nonfat Dry Milk/PBS) for 1 to 2.5 hours at ambient temperature (20-26° C.) or stored overnight at 2-8° C. Following blocking, the blocking solution is removed. Samples of plasma and standard anti-nicotine antibody solutions in various volumes of blocking solution (used as diluent) are added to the wells of the microtiter plates. Plates are covered and incubated at 37°(±2°) C for 45 (±5) minutes. The samples and standards are removed and the plates are washed and HRP-labeled goat anti-human $IgG_\gamma$ (prepared in blocking solution diluent) is added. Plates are incubated at 37° (±2°) C for 30 (±3) minutes. The chromogenic substrate (3,3',5,5'-tetramethylbenzidine) is prepared and added to the plates and incubated at ambient temperature (20-26° C.) for 15 (±1) minutes. The reaction is stopped with 1.0M phosphoric acid. The absorbance values of the wells in the plates are read at 450 nanometers. Based on the standard curve, the levels of anti-nicotine antibodies are calculated.

Clinical Study—A randomized, double-blind, clinical study was conducted with 301 human subjects. All subjects were heavy smokers—the average number of cigarettes smoked per day was 24, with no subject smoking less than 15 cigarettes per day. 201 subjects were treated with NicVAX® and 100 received placebo treatment. The design of the study is shown in FIG. 1. As shown in FIG. 1, two dosing schedules and two dosage levels of NicVAX® were tested. Placebos received phosphate buffered saline and alum. The clinical endpoint of the study was continuous abstinence from smoking during weeks 19-26 after first vaccination.

Under Schedule 1, 50 subjects were dosed intravenously with 400 µg or 200 µg of NicVAX® (and alum adjuvant) at 0, 6, 12 and 26 weeks. Under Schedule 2, 51 and 50 subjects were dosed with 400 µg or 200 µg of NicVAX® (and alum adjuvant) at 0, 4, 8, 16 and 26 weeks. For each dosing schedule, 50 placebo patients received PBS and alum. TQD=Target Quit Date, which was 1 week after the second dose. Subjects in the study were encouraged to quit smoking at the TQD. Subjects also received brief behavioral counseling at 5 visits before and after the TQD.

Figure 2A:
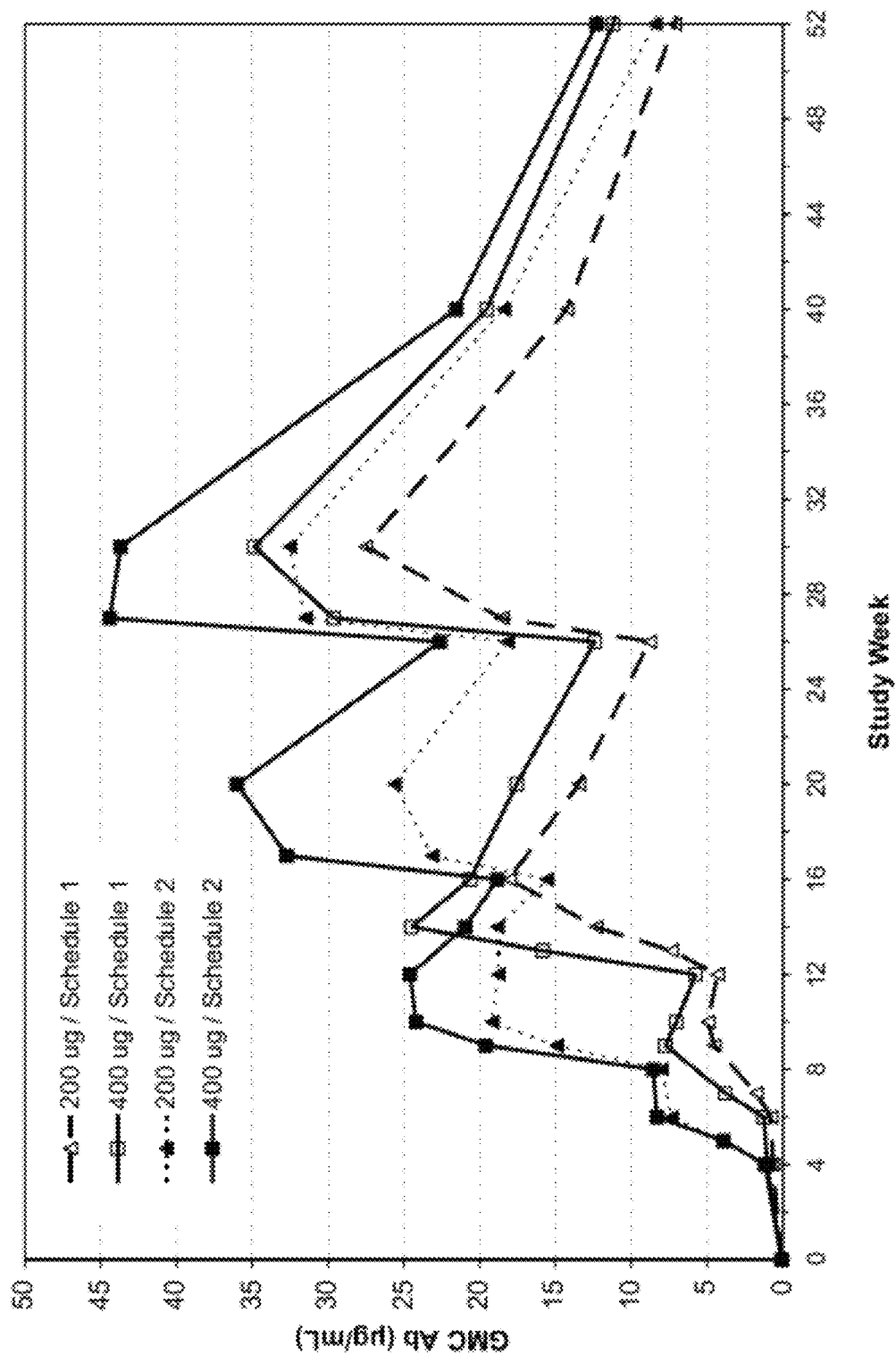
FIG. 2A shows the geometric mean concentration (GMC) of subject serum antibody levels (μg/ml) between 0 and 52 weeks of the subjects in the clinical study (Δ: 200 μg/Schedule 1; □: 400 μg/Schedule 1; ▲: 200 μg/Schedule 2; ■: 400 μg/Schedule 2).
Figure 2B:
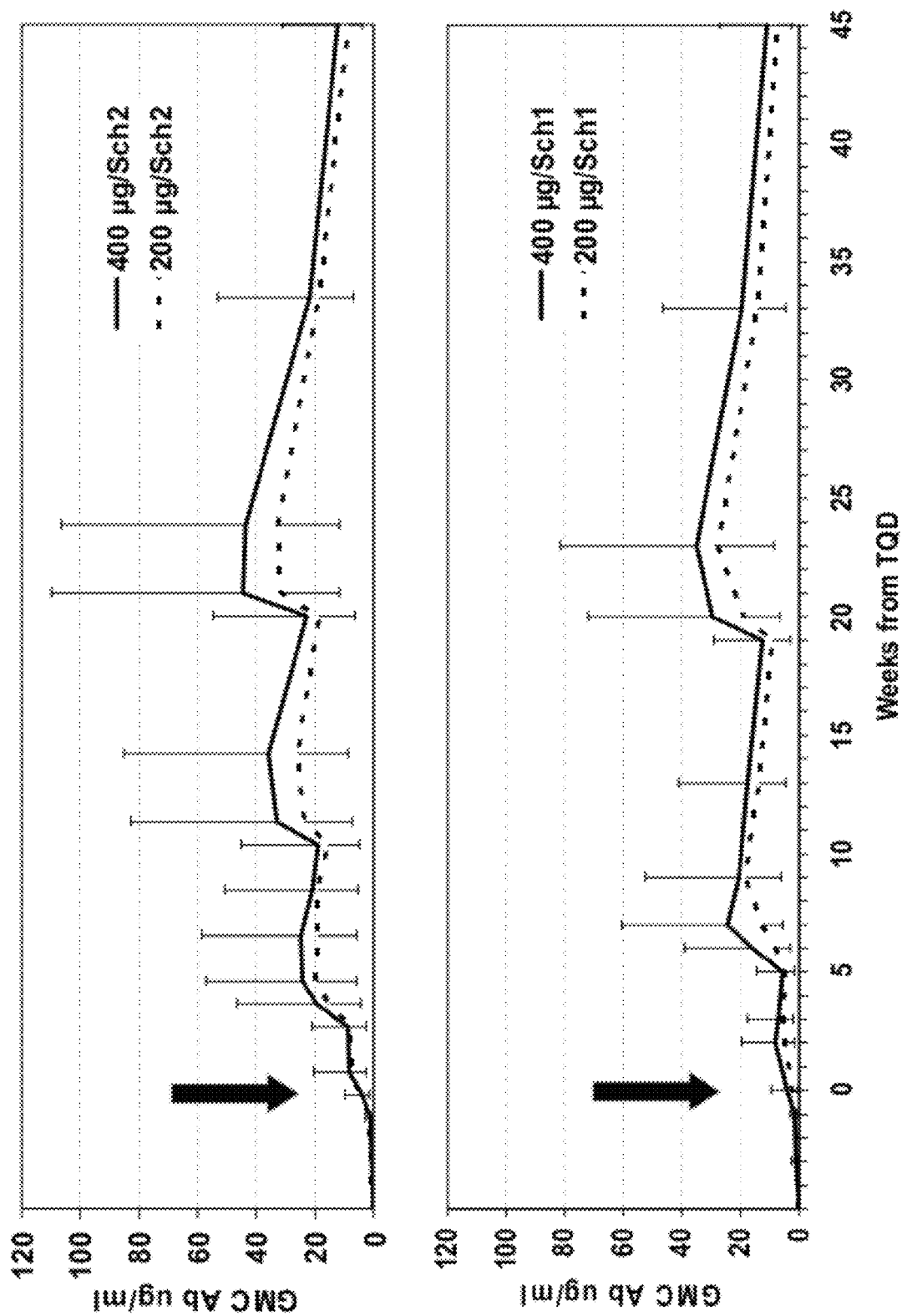
FIG. 2B shows the subject serum antibody levels (GMC Ab μg/ml) between 0 and 45 weeks following the target quit date. Error bars reflect individual antibody level variation.

FIGS. 2A and 2B show the antibody levels (µg/ml) of the subjects in the Schedule 1 and Schedule 2, 200 µg/ml and 400 µg/ml groups, between 0 and 52 weeks (FIGS. 2A & 2B). The data show that Schedule 2 achieves higher serum antibody levels earlier, and that Schedule 2 serum antibody levels remain higher than the Schedule 1 antibody levels throughout the 52-week study period. The error bars in FIG. 2B also illustrate the subject-to-subject variability of antibody responses. The present invention helps manage that variability of antibody response by providing an individualized determination of an advantageous time to quit smoking, based on the subject's own antibody levels.

FIG. 3 shows the rates of continuous abstinence in the various treatment groups. Continuous abstinence was measured as abstinence from smoking from two weeks after the target quit date until 6, 9 or 12 months following the first injection of NicVAX®. Electronic diaries recorded cigarette use daily for the first six months, and then weekly for the second six months. Carbon monoxide levels exhaled by subjects were measured and levels of ≦8 ppm confirmed continuous abstinence. These data were analyzed on an intent to treat (ITT) basis; volunteers who dropped out from the study or missing data points are counted as smokers. The percentages were derived by dividing the number of quitters, who maintained abstinence for the 20-week; 34-week and 44 week periods respectively by the number of individuals recruited and entered into the study. The data show that Schedule 2 with the 400 µg NicVAX® dose resulted in the highest abstinence rates.

FIG. 4A demonstrates that those subjects with the highest antibody levels also had the highest 12-month continuous abstinence rates. The "high antibody" group includes the top 30% of antibody responders among all subjects irrespective of immunization schedule or dose, based on the area under the curve (AUC) of serum antibody levels for the first 6 months. The "low antibody" group includes the remaining 70% of NicVAX® vaccinated subjects. The data show that 25% of the "high antibody" group (across all schedules/dosages) showed continuous abstinence at 6 months, as compared to only 10% of the low antibody group and 13% of the placebo group. Thus, subjects in the "high antibody" group had a probability of continuous abstinence at 6 months that was about 2 times greater than that of the placebo group. The data also show that 16% of the "high antibody" group (across all schedules/dosages) showed continuous abstinence at 12 months, as compared to only 8% of the low antibody group and 6% of the placebo group. Thus, subjects in the "high antibody" group had a probability of continuous abstinence at 12 months that was greater than 2.5 times greater than that of the placebo group.

Figure 4B:
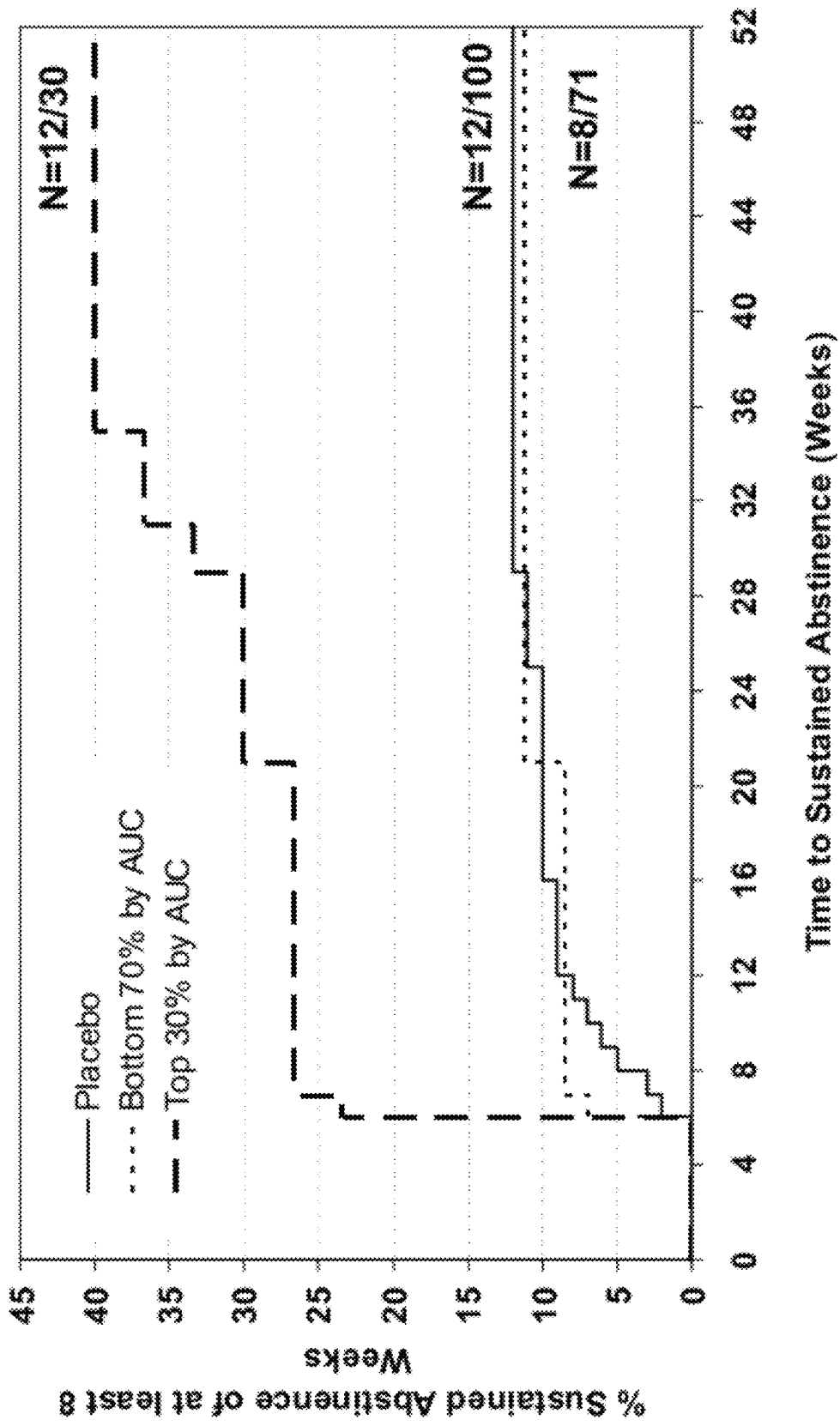
FIG. 4B shows a time-to-onset analysis of sustained abstinence of at least 8 weeks as a function of antibody level at four months for NicVAX subjects undergoing a 5 injection regimen (—: placebo; . . . : bottom 70% by AUC; - - - : Top 30% by AUC). This analysis demonstrates a highly significant result where the top antibody group attains 40% abstinence at one-year.

In FIG. 4B, a Cox proportional hazard analysis of quitting smoking by 12 months (as measured as at least 8 weeks of continuous abstinence by 12 months) showed a 40% quit rate in the "high antibody" group versus a 12% quit rate in the placebo group (across all subjects receiving 5 injections, Schedule 2).

Figure 5:
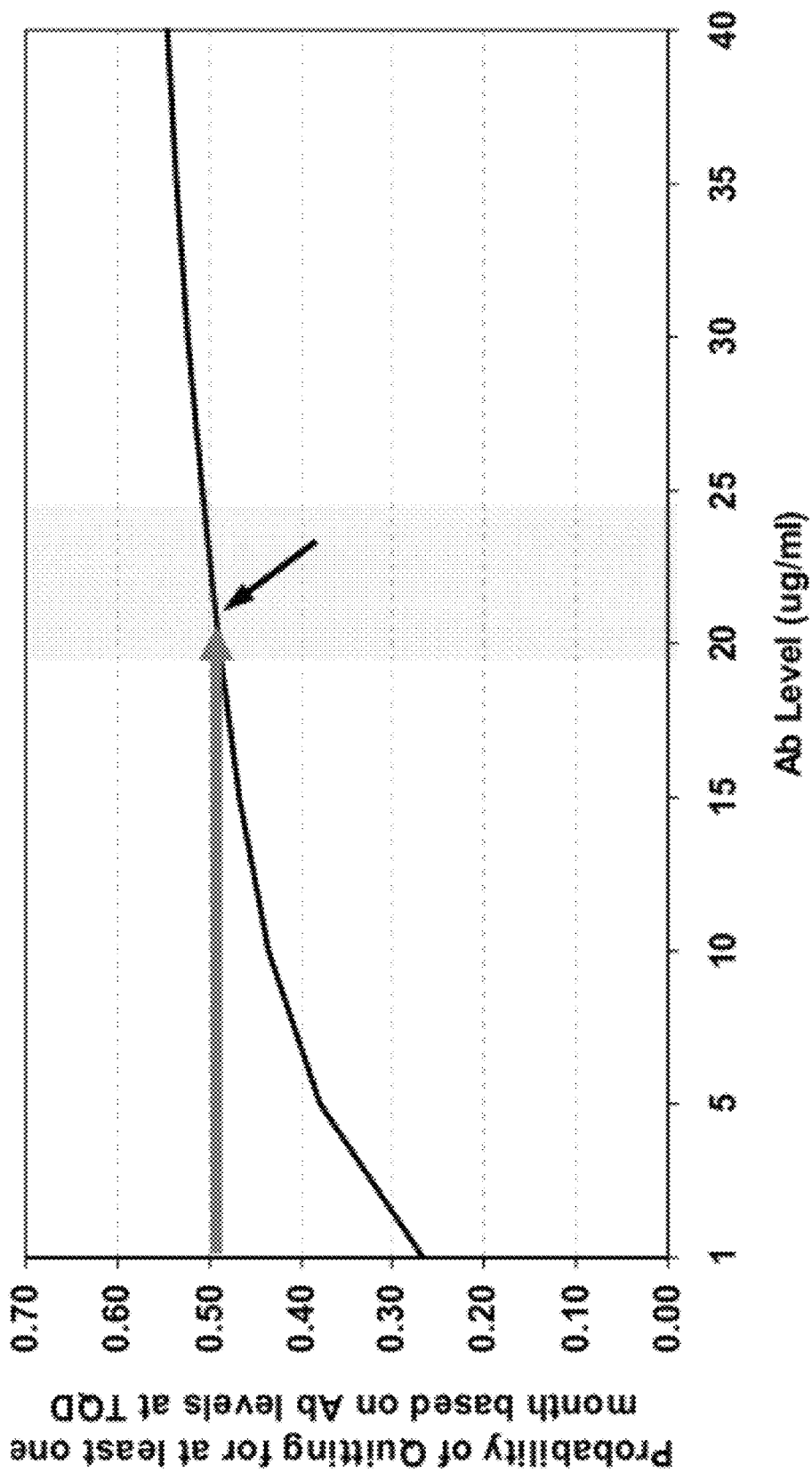
FIG. 5 shows the probability of quitting smoking for at least four weeks, based on subject serum antibody levels at the target quit date (TQD), further illustrating a target anti-nicotine antibody level (20-25 μg/ml) that supports about a 50% chance of quitting for one month or more.

FIG. 5 shows the probability of quitting smoking for at least four weeks, based on subject serum antibody levels at the target quit date (TQD), and on the results of the clinical trial. A threshold effect of antibody level on smoking cessation is observed beginning at serum antibody levels of about 6 µg/ml, with a 50% chance of quitting smoking for at least four weeks being observed beginning at serum antibody levels of about 20-25 µg/ml.

Figure 6A:
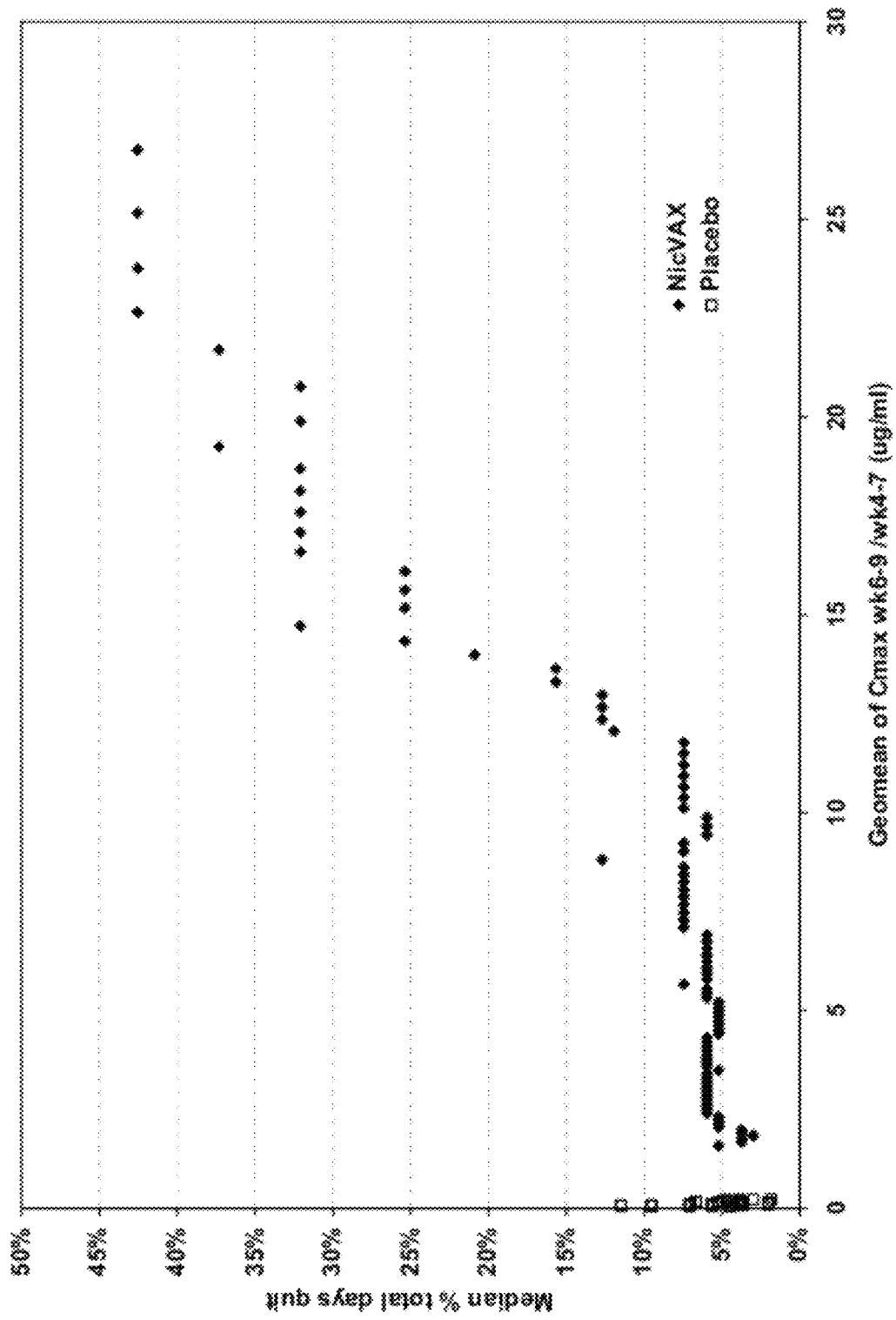
FIG. 6 shows the antibody threshold determination for a sliding tertile of 49 subjects (□—placebo; ♦—NicVAX®). The figure plots median (FIG. 6A) and mean (FIG. 6B) percent total days quit from the target quit date (TQD) to six months versus serum antibody levels within one month of TQD.
Figure 6B:
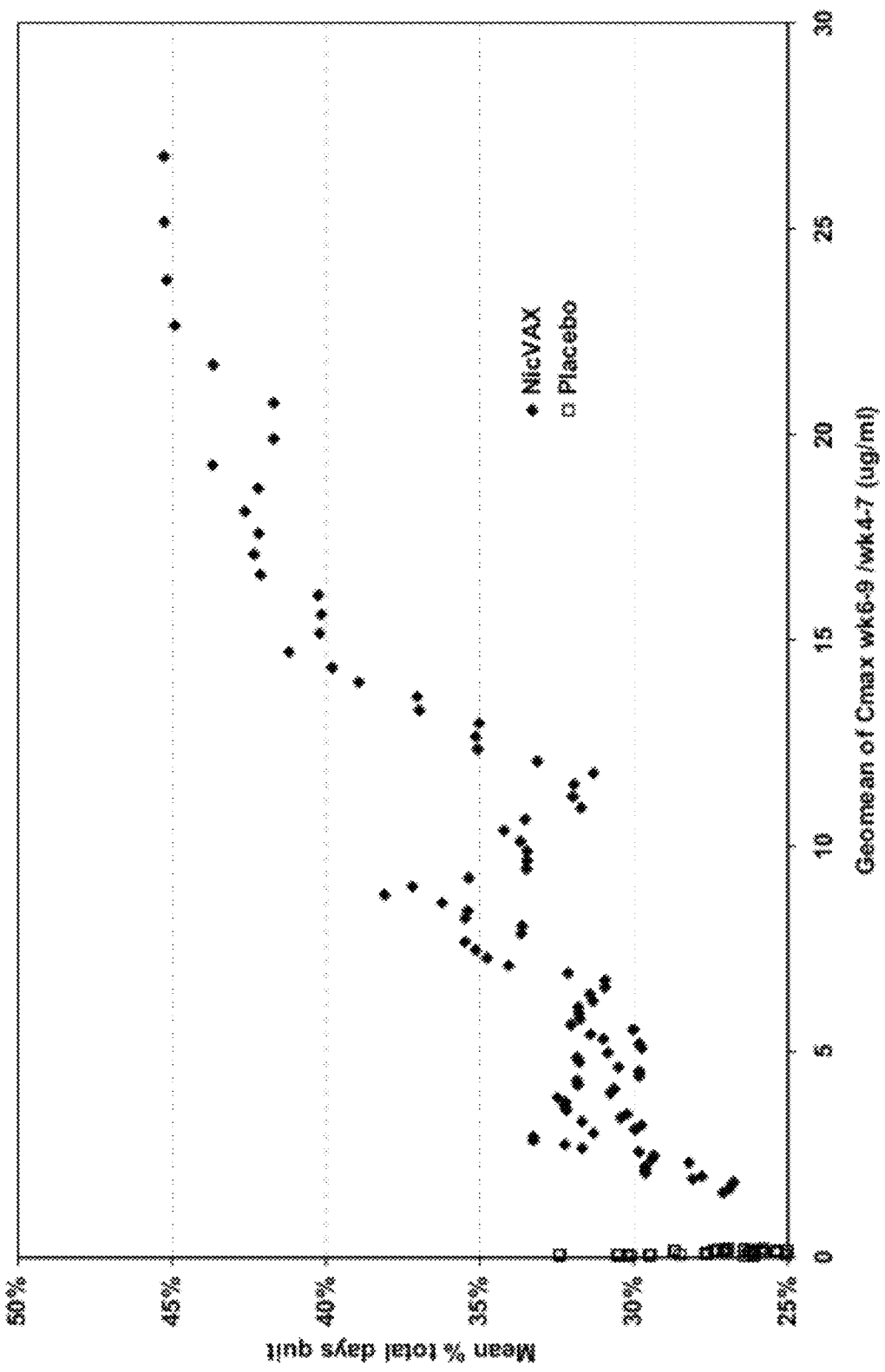

FIGS. 6A and 6B shows the antibody threshold determination for a sliding tertile of 49 subjects. A threshold effect of antibody level (measured within one month of the target quit date) on smoking cessation (as measured by the median and mean % total cumulative days quit during the first 6 months of the study) is observed beginning at serum antibody levels of about 6 µg/ml, with further improved smoking cessation observed for subjects with serum antibody levels of at least about 10-12 µg/ml, and still further improved smoking cessation observed for subjects with serum antibody levels of at least about 20-25 µg/ml, with all antibody levels being measured within one month of the target quit date.

Serum anti-nicotine antibody levels of subjects in the high antibody (top 30% by AUC over 6 months) group were measured. The geometric mean concentration of the anti-nicotine antibody levels at the TQD was 19.4 µg/ml for this group.

Serum anti-nicotine antibody levels of those subjects in the high antibody group (top 30% by AUC over 6 months) who quit smoking for at least the first four weeks following the TQD were measured. The geometric mean concentration of anti-nicotine antibody levels for these subjects at the TQD was 23.3 µg/ml.

Of the 17 subjects who had the highest antibody levels (>50 µg/ml) at 4 months from the study start date, 10 subjects remained quit during the last 8 weeks (weeks 45-52) of the study. These subjects had a geometric mean concentration of anti-nicotine antibody levels at the TQD of 23.6 µg/ml.

The study also revealed that subjects in the high antibody group (top 30% at the TQD) who achieved long term quit success (e.g., 12 months of continuous abstinence) had anti-nicotine antibody levels at the TQD that were about 1.78 times the number of cigarettes smoked the day before the target quit date (based on the average number of cigarettes smoked during the week prior to the target quit date).

Further analyses determined that dose dependence of smoking cessation and long-term abstinence could be demonstrated based on the results of the study.

Dose Dependence

Figure 7:
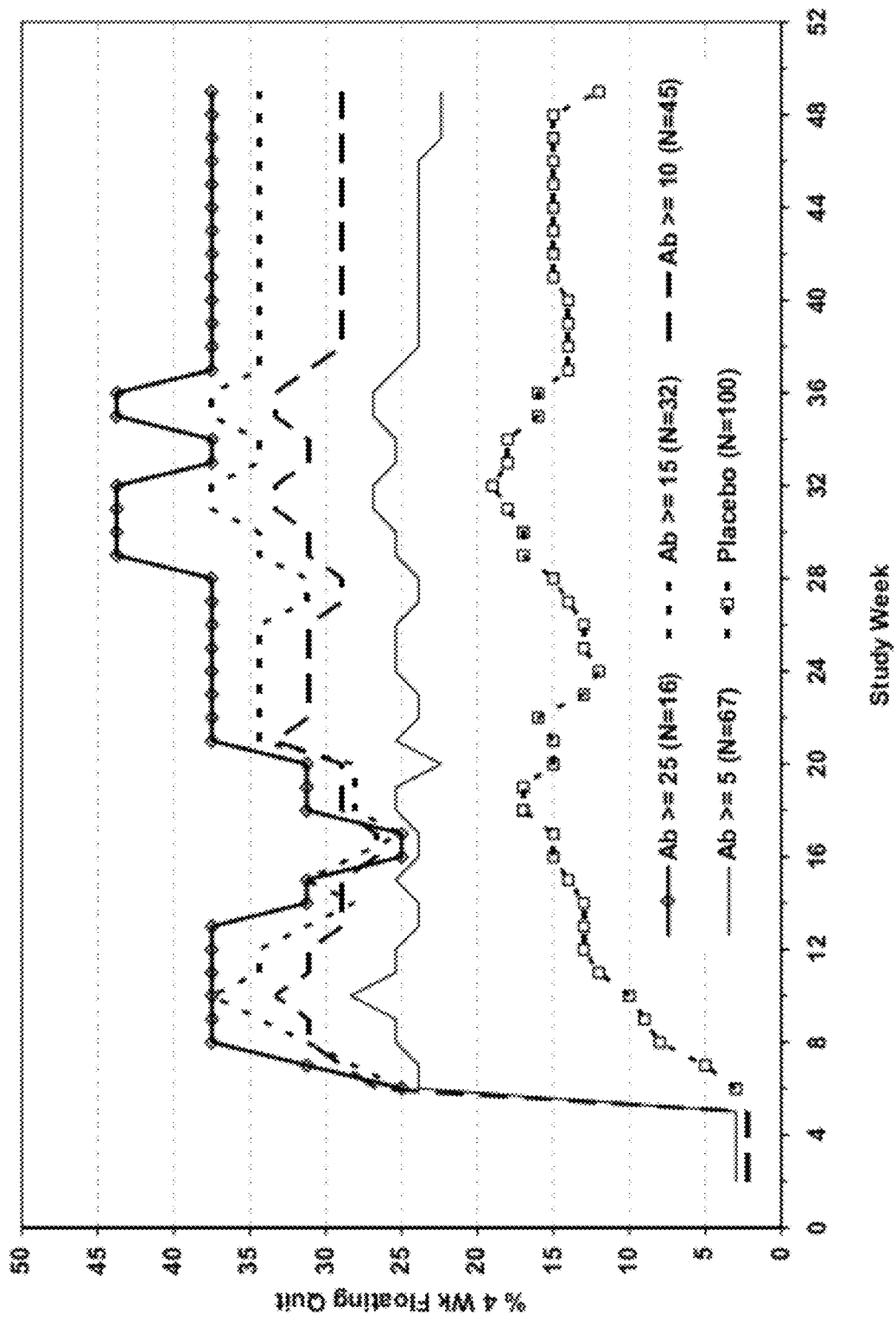
FIG. 7 depicts rates of smoking cessation in monthly increments for each week in the study—a floating 4-week quit window—from week 1 to week 4, from week 2 to week 5, from week 49 to 52, as a function of serum anti-nicotine antibody levels in the Schedule 2 study subjects at the target quit date (♦: Ab≧25 (N=16); - - - : Ab≧15 (N=32); —— —: Ab≧10 (N=45); ——: Ab≧(N=67); □: Placebo (N=100)).

FIG. 7 depicts rates of smoking cessation in monthly increments—a floating 4-week quit window—as a function of serum anti-nicotine antibody levels in the study subjects at the target quit date. Data is shown for subjects with serum anti-nicotine antibody levels of at least 5 µg/mL (n=67), at least 10 µg/mL (n=45), at least 15 µg/mL (n=32), and at least 25 µg/mL (n=16), and for placebo subjects (n=100). The results indicate a strong correlation between the percentage of quitters, i.e., smoking cessation, and various threshold levels of anti-nicotine antibody. Thus, for example, at any given time period, about 25% of subjects with serum anti-nicotine antibody levels of at least 5 µg/ml at the target quit date quit smoking, while close to 30% of subjects with serum anti-nicotine antibody levels of at least 10 µg/ml quit smoking, up to about 35% of subjects with serum anti-nicotine antibody levels of at least 15 µg/ml quit smoking, and greater than 35% of subjects with serum anti-nicotine antibody levels of at least 25 µg/ml quit smoking. This analysis shows that higher threshold levels of anti-nicotine antibody at the target quit date lead to increased smoking cessation rates of at least one month in duration. It also shows that the results are somewhat independent of counseling (e.g. after week 16). Further, the results show that lower smoking cessation rates, i.e., smoking relapses, are observed during the time frames when antibody levels are in decline, such as between weeks 12 to 16.

Long Term Abstinence

Figure 8:
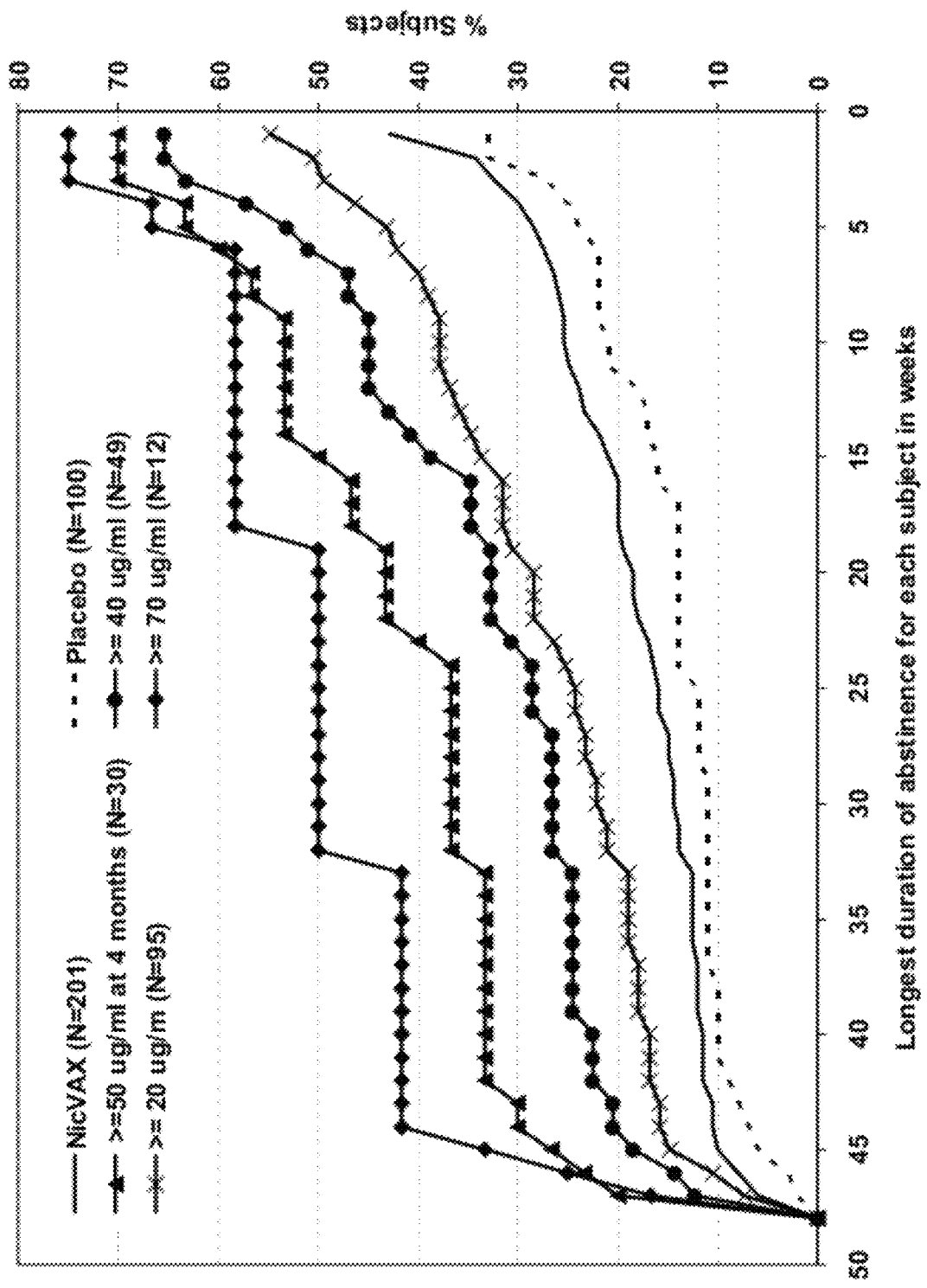
FIG. 8 illustrates the longest period of continuous abstinence as correlated with serum anti-nicotine antibody levels at four months (—: NixVAX (N=201; ▲: ≧50 μg/mL at 4 months (N=30); ●: ≧40 μg/mL (N=49); X: ≧20 μg/mL (N=95); ♦: ≧70 μg/mL (N=12); - - -: placebo (N=100)).

FIG. 8 depicts the longest period of continuous abstinence that is correlated with various serum anti-nicotine antibody levels at four months (after the fourth vaccine dose). Data is shown for subjects with serum anti-nicotine antibody levels of at least 70 µg/mL (n=12), at least 50 µg/mL (n=30), at least 40 µg/mL (n=49), and for placebo subjects (n=100). Data also is shown for all vaccinated subjects (NicVAX, N=201), all vaccinated subjects with serum anti-nicotine antibody levels less than 50 µg/mL (n=171), and all vaccinated subjects with serum anti-nicotine antibody greater than 20 µg/mL. For example, 40% of subjects who had serum anti-nicotine antibody levels of at least 70 µg/mL abstained from smoking for 44 weeks, compared to about 30% of subjects who had serum anti-nicotine antibody levels of at least 50 µg/mL, and 20% of subjects who had serum anti-nicotine antibody levels of at least 40 µg/mL. (The geometric mean antibody level at the target quit date for the subjects in the 70 µg/mL group was 36 µg/mL). These results illustrate that antibody-levels are correlated with the duration of abstinence achieved by an individual.

Figure 9:
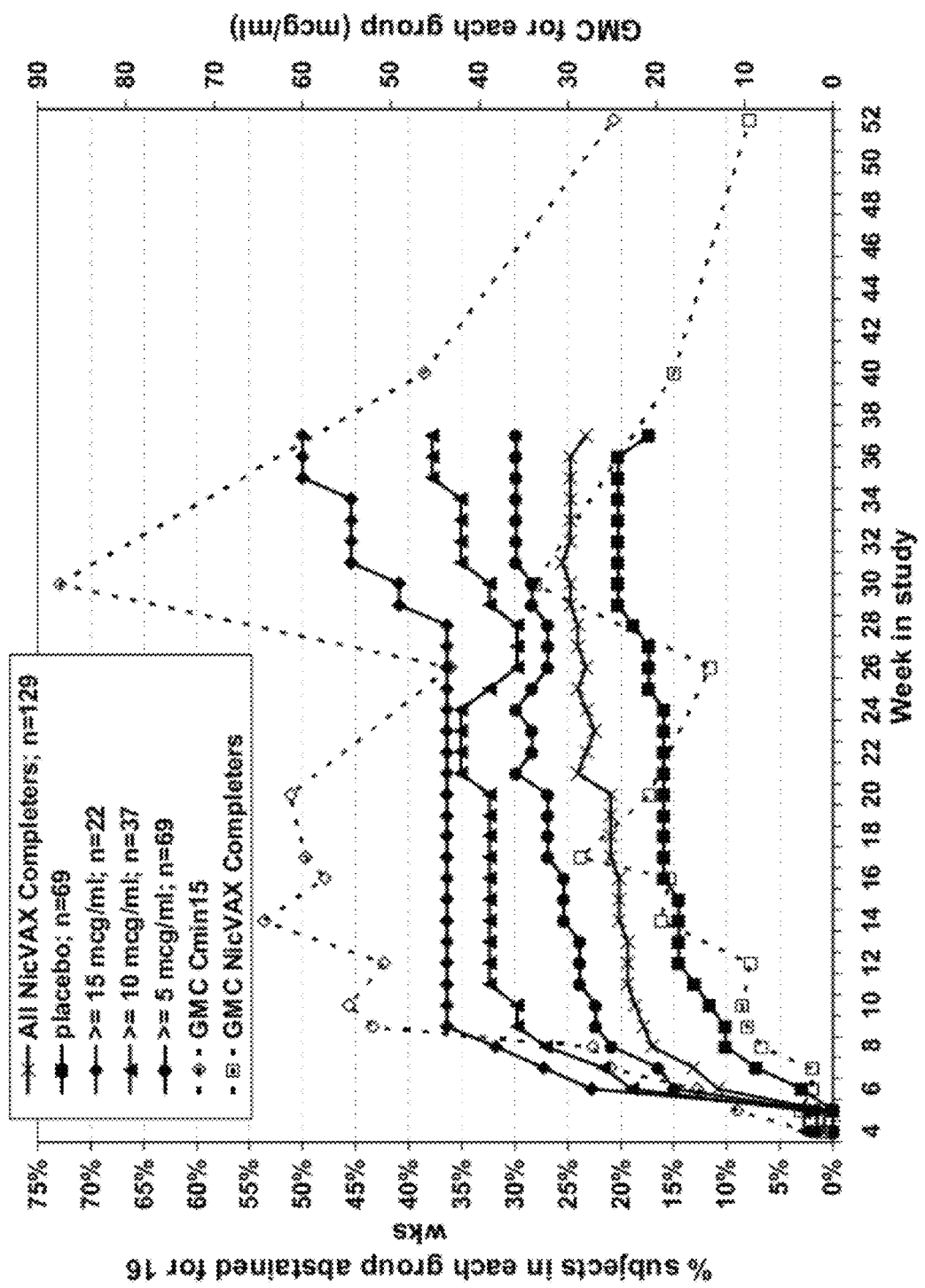
FIG. 9 depicts rates of smoking cessation in four month increments for each week in the study—a floating 16-week abstinence window—from week 1 to week 16, from week 2 to week 17, from week 37 to 52, as a function of the minimum serum anti-nicotine antibody levels ($C_{min}$) observed in the study subjects as measured between the target quit date and six months (weeks 9 to 26, inclusive) (X: all NicVAX completers (N=129); ■: placebo (N=69); ♦: ≧15 μg/mL (N=22); ▲: ≧10 μg/mL (N=37); ●: ▲: ≧5 μg/mL (N=69); ◇: GMC $C_{min}15$; □: GMC NicVAX completers). This analysis demonstrates that a high four month abstinence rate is associated with $C_{min}$ levels of at least 15 μg/mL.

FIG. 9 illustrates that the percentage of subjects that achieve long-term abstinence, e.g., at least 16 weeks of continuous abstinence, over the course of the study is directly correlated with minimum serum anti-nicotine antibody levels observed between the target quit date and six months. In FIG. 9, data is shown for subjects with minimum serum anti-nicotine antibody levels of at least 5 µg/mL (n=69), at least 10 µg/mL (n=37), and at least 15 µg/mL (n=22), with the percentage of subjects that achieve long-term abstinence (e.g., at least 16 weeks continuous abstinence) increasing with each antibody level. Data also is shown for placebo subjects (n=69) and all vaccinated subjects (n=129), and the geometric mean of the Cmin levels for each of the 5 µg/mL, 10 µg/mL, and 15 µg/mL groups, and for the vaccinated subjects as a whole, also is shown. These results illustrate the advantages of maintaining minimum antibody levels and the correlation between minimum antibody levels and the ability to achieve long-term abstinence (e.g., at least 16 weeks continuous abstinence).

We claim:

1. A method for counseling a subject who has been administered with a nicotine immunogenic composition, on whether it is an advantageous time for the subject in need thereof to quit smoking, comprising
   (a) measuring the level of anti-nicotine antibodies in serum from the subject; and
   (b) counseling the subject that it is an advantageous time to quit smoking if the subject's serum anti-nicotine antibody levels are at or above a predetermined first specified threshold level of serum anti-nicotine antibodies and/or that it is not an advantageous time to quit smoking if the subject's measured level of serum anti-nicotine antibody levels are below the predetermined first specified threshold level of serum anti-nicotine antibodies, wherein said first specified threshold level of serum anti-nicotine antibodies is at least about 6 ug/ml.

2. The method of claim 1, wherein the first specified threshold level of serum anti-nicotine antibodies is directly correlated with the subject's degree of addiction to nicotine as measured by at least one of the following factors:
   (i) the degree of addiction, as measured by the baseline smoking level;
   (ii) the degree of addiction, as measured by the number of cigarettes smoked immediately prior to the measurement of anti-nicotine antibodies;
   (iii) the number of previous quit attempts made within a certain period of time;
   (iv) how soon in the morning after awakening on a given day the subject craves or actually lights the first cigarette or consumes other form(s) of nicotine.

3. The method of claim 1, further comprising, prior to step (b), determining the subject's number of cigarettes smoked per day, wherein the first specified threshold level of serum anti-nicotine antibodies is correlated with the subject's number of cigarettes smoked per day.

4. The method of claim 3, wherein the first specified threshold level of serum anti-nicotine antibodies is selected from the group consisting of at least about 25 µg/ml, at least about 30 µg/ml, at least about 35 µg/ml, at least about 40 µg/ml, at least about 45 µg/ml, and at least about 50 µg/ml, for subjects with a number of cigarettes smoked per day of 30 or greater, or is from about 1.5 to about 2.0 times the subject's number of cigarettes smoked per day.

5. The method of claim 1, wherein the first specified threshold level of serum anti-nicotine antibodies is directly correlated with the number of doses of a nicotine immunogenic composition that the subject has received prior to the measuring of the level of anti-nicotine antibodies.

6. The method of claim 5, wherein the first specified threshold anti-nicotine antibody level is selected from at least 25 µg/ml for up to two prior doses, at least 50 µg/ml for three prior doses, at least 75 µg/ml for four prior doses, and at least 100 µg/ml for five prior doses.

7. The method of claim 1, further comprising counseling the subject to have administered a nicotine immunogenic composition, if the subject's serum anti-nicotine antibody levels are not at or above a second specified threshold level of serum anti-nicotine antibodies, wherein said second specified threshold level of serum anti-nicotine antibodies is at least about 6 ug/ml.

8. The method of claim 1, further comprising administering to the subject a nicotine immunogenic composition, if the subject's serum anti-nicotine antibody levels are not at or above a second specified threshold level of serum anti-nicotine antibodies, wherein said second specified threshold level of serum anti-nicotine antibodies is at least about 6 ug/ml.

9. The method of claim 8, wherein the second specified threshold level is selected from the group consisting of at least about 10 μg/ml, at least about 15 μg/ml, at least about 20 μg/ml, at least about 25 μg/ml, at least about 30 μg/ml, at least about 35 μg/ml, at least about 40 μg/ml, at least about 45 μg/ml, and at least about 50 μg/ml, or is from about 1.5 to about 2.0 times the subject's number of cigarettes smoked per day.

10. The method of claim 8, wherein the nicotine immunogenic composition comprises a nicotine-carrier conjugate comprising 3'aminomethylnicotine.

11. The method of claim 1, further comprising, prior to step (a), administering to the subject a nicotine immunogenic composition.

12. The method of claim 11, wherein the nicotine immunogenic composition comprises a nicotine-carrier conjugate comprising 3'aminomethylnicotine.

13. The method of claim 1, wherein the first specified threshold level of serum anti-nicotine antibodies is selected from the group consisting of at least about 10 μg/ml, at least about 15 μg/ml, at least about 20 μg/ml, and at least about 25 μg/ml.

14. The method of claim 1, wherein the first specified threshold level of serum anti-nicotine antibodies is selected from the group consisting of up to at least about 25 μg/ml, at least about 30 μg/ml, at least about 35 μg/ml, at least about 40 μg/ml, at least about 45 μg/ml, and at least about 50 μg/ml.

15. The method of claim 1, wherein step (a) is performed using a method selected from the group consisting of an enzyme-linked immunosorbent assay (ELISA), a radioimmunoassay, spectroscopic methods, quantum dots, fluorescence methods, bioluminescence methods, chromatographic methods and mass spectrometry.

16. The method of claim 1, further comprising, prior to step (b), transforming data related to at least one factor selected from the group consisting of the subject's degree of nicotine addiction and the number of doses of a nicotine immunogenic composition the subject has received, into a first specified threshold serum anti-nicotine antibody level.

17. A method for determining whether it is an advantageous time for a subject who has been administered with a nicotine immunogenic composition and in need thereof to quit smoking, comprising:
 (a) measuring the level of anti-nicotine antibodies in serum from said subject; and
 (b) determining that it is an advantageous time for a subject to quit smoking if the measured level of serum anti-nicotine antibodies is at or above a predetermined first specified threshold level of serum anti-nicotine antibodies or that it is not an advantageous time for a subject to quit smoking if the measured level of serum anti-nicotine antibodies is below the predetermined first specified threshold level of serum anti-nicotine antibodies serum, wherein said first specified threshold level of serum anti-nicotine antibodies is at least about 6 ug/ml.

18. The method of claim 17, further comprising, prior to step (b):
 (a') transforming data related to at least one factor selected from the group consisting of the subject's degree of nicotine addition and the number of doses of a nicotine immunogenic composition the subject has received, into said first specified threshold level of serum anti-nicotine antibodies.

* * * * *